US010119448B2

(12) United States Patent
Kidokoro et al.

(10) Patent No.: US 10,119,448 B2
(45) Date of Patent: Nov. 6, 2018

(54) FAULT DIAGNOSIS APPARATUS FOR EXHAUST GAS PURIFICATION SYSTEM

(71) Applicant: TOYOTA JIDOSHA KABUSHIKI KAISHA, Toyota-shi, Aichi-ken (JP)

(72) Inventors: Toru Kidokoro, Hadano (JP); Makoto Ogiso, Mishima (JP); Kenji Furui, Sunto-gun (JP); Arifumi Matsumoto, Gotenba (JP); Takeru Shirasawa, Susono (JP)

(73) Assignee: Toyota Jidosha Kabushiki Kaisha, Toyota-shi, Aichi-ken (JP)

(*) Notice: Subject to any disclaimer, the term of this patent is extended or adjusted under 35 U.S.C. 154(b) by 168 days.

(21) Appl. No.: 15/359,712

(22) Filed: Nov. 23, 2016

(65) Prior Publication Data

US 2017/0152784 A1 Jun. 1, 2017

(30) Foreign Application Priority Data

Nov. 27, 2015 (JP) ................................ 2015-232467

(51) Int. Cl.
*B01D 53/94* (2006.01)
*F01N 11/00* (2006.01)
(Continued)

(52) U.S. Cl.
CPC .......... *F01N 11/00* (2013.01); *B01D 46/0027* (2013.01); *B01D 53/9418* (2013.01);
(Continued)

(58) Field of Classification Search
CPC .... B01D 46/0027; B01D 53/92; B01D 53/94; B01D 53/9418; B01D 53/9431;
(Continued)

(56) References Cited

U.S. PATENT DOCUMENTS 9,133,752 B2 * 9/2015 Jun ........................... F01N 9/00
2013/0064718 A1 * 3/2013 Onodera ............... F01N 3/2066 422/108

(Continued)

FOREIGN PATENT DOCUMENTS

JP 2015-010589 1/2015

OTHER PUBLICATIONS

Friedemann Schrade, et al., "Physico-Chemical Modeling of an Integrated SCR on DPF (SCR/DPF) System", *SAE International Journal of Engines*, Aug. 2012, vol. 5, No. 3, pp. 958-974.

*Primary Examiner* — Nguyen Ha

(74) *Attorney, Agent, or Firm* — Finnegan, Henderson, Farabow, Garrett & Dunner, LLP

(57) ABSTRACT

Embodiments of the present disclosure may improve the accuracy of diagnosis in diagnosing whether an exhaust gas purification system having an SCR filter is faulty. It is determined that the exhaust gas purification system is faulty if the NOx removal rate with the SCR filter calculated using a measurement value of an NOx sensor is lower than or equal to a predetermined criterion removal rate. In the apparatus, a differential pressure change rate defined as the increase in a converted differential pressure value per unit increase in the filter PM deposition amount is calculated. The value of the criterion removal rate is set higher when the differential pressure change rate at the time when the measurement value of the NOx sensor is obtained is lower than a predetermined threshold than when the differential pressure change rate is higher than or equal to the predetermined threshold.

6 Claims, 11 Drawing Sheets

ACCELERATOR POSITION SENSOR
CRANK POSITION SENSOR
ECU

(51) Int. Cl.

| | |
|---|---|
| ***B01D 46/00*** | (2006.01) |
| ***F01N 3/035*** | (2006.01) |
| ***F01N 3/20*** | (2006.01) |
| ***G01N 15/08*** | (2006.01) |
| *G01N 15/00* | (2006.01) |

(52) U.S. Cl.

CPC ..... *B01D 53/9431* (2013.01); *B01D 53/9495* (2013.01); *F01N 3/035* (2013.01); *F01N 3/208* (2013.01); *F01N 3/2066* (2013.01); *G01N 15/0826* (2013.01); *B01D 2251/2062* (2013.01); *B01D 2255/911* (2013.01); *B01D 2258/012* (2013.01); *B01D 2279/30* (2013.01); *F01N 2550/02* (2013.01); *F01N 2560/026* (2013.01); *F01N 2560/08* (2013.01); *F01N 2610/02* (2013.01); *F01N 2900/1602* (2013.01); *F01N 2900/1621* (2013.01); *G01N 2015/0046* (2013.01); *G01N 2015/084* (2013.01)

(58) Field of Classification Search

CPC ................ B01D 53/9495; B01D 53/96; B01D 2251/2062; B01D 2258/012; B01D 2279/30; F01N 3/035; F01N 3/208; F01N 3/2066; F01N 11/00; F01N 2550/02; F01N 2560/026; F01N 2560/08; F01N 2610/02; F01N 2900/1602; F01N 2900/1621; G01N 15/0826; G01N 2015/0046; G01N 2015/084

See application file for complete search history.

(56) References Cited

U.S. PATENT DOCUMENTS

| | | | | |
|---|---|---|---|---|
| 2015/0315950 | A1* | 11/2015 | Hagimoto | F01N 3/023<br>73/114.75 |
| 2017/0204770 | A1* | 7/2017 | Kimura | F01N 3/2839 |
| 2018/0023430 | A1* | 1/2018 | Higashiyama | F01N 3/021 |

* cited by examiner

10
ECU
ACCELERATOR POSITION SENSOR
CRANK POSITION SENSOR
7
8
1
2
3
4
5
40
41
50
51
51a
52
53
54
55
56
57
58
59

110
PM DEPOSITION AMOUNT CALCULATION UNIT
DISCHARGED PM QUANTITY
TRAPPED PM QUANTITY CALCULATION UNIT
111
TRAPPED PM QUANTITY
FILTER TEMPERATURE
INFLOWING $O_2$ CONCENTRATION
INFLOWING $NO_2$ CONCENTRATION
PREVIOUS DEPOSITION AMOUNT VALUE
OXIDIZED PM QUANTITY CALCULATION UNIT
112
OXIDIZED PM QUANTITY
+
-
+
FILTER PM DEPOSITION AMOUNT

FAULT DIAGNOSIS APPARATUS FOR EXHAUST GAS PURIFICATION SYSTEM

TECHNICAL FIELD

The present disclosure relates to a fault diagnosis apparatus for an exhaust gas purification apparatus that purifies the exhaust gas of an internal combustion engine.

BACKGROUND ART

It is known in prior art to provide an SCR filter made up of a filter and an SCR catalyst (selective catalytic reduction NOx catalyst) supported on the filter in an exhaust passage of an internal combustion engine. The SCR filter has a capability of reducing NOx in the exhaust gas by using ammonia as reducing agent. The filter has the function of trapping particulate matter (which will be hereinafter referred to as "PM") in the exhaust gas. In an exhaust gas purification system equipped with such an SCR filter, ammonia serving as reducing agent is supplied to the SCR filter by an ammonia supply device provided in the exhaust passage.

Patent Literature 1 discloses a technology pertaining to a fault diagnosis apparatus for an exhaust gas purification system equipped with an SCR catalyst provided in the exhaust passage. In the technology disclosed in Patent Literature 1, a certain threshold and a correction coefficient for fault diagnosis is set on the basis of intermediate characteristics between purification characteristics in the case where the exhaust gas system is sound and purification characteristics in the case where the exhaust gas purification system is faulty. The correction coefficient thus set is used to correct the NOx removal rate that is calculated using the quantity of NOx flowing out of the SCR catalyst as a parameter. The NOx removal rate after the correction is compared with the threshold to diagnose whether or not the exhaust as purification system is faulty.

Non-Patent Literature 1 teaches that increases in the amount of PM deposited in an SCR filter make the ammonia adsorption amount defined as the amount of ammonia adsorbed in an SCR catalyst supported on the SCR filter more apt to increase.

CITATION LIST

Patent Literature

PTL 1: Japanese Patent Application Laid-Open No. 2015-010589

Non-Patent Literature

NON-PTL 1: "Physico-Chemical Modeling of an Integrated SCR on DPF (SCR/DPF) System", SAE International Journal of Engines, August 2012 vol. 5 no. 3, 958-974

SUMMARY

Technical Problem

It is known in prior art to diagnose whether or not an exhaust gas purification system equipped with an SCR filter is faulty on the basis of the NOx removal rate with the SCR filter (namely, the rate of the quantity of NOx reduced in the SCR filter to the quantity of NOx flowing into the SCR filter). As described in the aforementioned prior art literature, the ammonia adsorption amount in the SCR catalyst supported on the SCR filter may be affected by the state of deposition of PM in the SCR filter to change. A change in the ammonia adsorption amount in the SCR catalyst will lead to a change in the NOx removal rate with the SCR filter. Therefore, to make a diagnose as to fault of the exhaust gas purification system on the basis of the NOx removal rate with the SCR filter with high accuracy, it is necessary to take into account the effect of the state of deposition of PM in the SCR filter.

The present disclosure has been made in view of the above-described problem, and embodiments of the present disclosure may improve the accuracy of diagnosis as to whether or not an exhaust gas purification system equipped with an SCR filter is faulty.

Solution to Problem

As an SCR filter traps PM in the exhaust gas, the trapped PM is deposited in the SCR filter gradually. In the SCR filter, PM is firstly deposited in partition walls of the SCR filter, specifically, in micro-pores in the partition walls. After the amount of PM deposited in the partition walls reaches its upper limit, PM is deposited on the surface of partition walls. In the following, deposition of PM in the partition walls of the SCR filter will be sometimes referred to as "in-wall PM deposition", and the period during which the in-wall PM deposition progresses will be sometimes referred to as the "in-wall PM deposition period". The amount of PM deposited in the partition walls of the SCR filter will be sometimes referred to as the "in-wall PM deposition amount". Furthermore, deposition of PM on the surface of partition walls of the SCR filter will be sometimes referred to as "surface PM deposition", and the period during which the surface PM deposition progresses will be sometimes referred to as the "surface PM deposition period". The amount of PM deposited on the surface of the partition walls of the SCR filter will be sometimes referred to as the "surface PM deposition amount".

As described above, it has been conventionally considered that increases in the amount of PM deposited in the SCR filter tend to make the amount of ammonia adsorbed in an SCR catalyst supported on the SCR filter more apt to increase. However, details of relationship between the state of deposition of PM in the SCR filter and the tendency of increase of the ammonia adsorption amount in the SCR catalyst had not been known previously. The inventors of the present disclosure discovered the tendency that while the ammonia adsorption amount in the SCR catalyst is more apt to increase when the in-wall PM deposition amount in the SCR filter is large than when the in-wall PM deposition amount is small, increases or decreases in the surface PM deposition amount in the SCR filter have little effect on increases or decreases in the ammonia adsorption amount in the SCR catalyst. It is considered that the reason why the ammonia adsorption amount in the SCR catalyst is more apt to increase when the in-wall PM deposition amount in the SCR filter is large than when the in-wall PM deposition amount is small is that increases in the in-wall PM deposition amount lead to increases in the saturated ammonia adsorption amount of the SCR catalyst, leading to decreases in the quantity of ammonia desorbed from the SCR catalyst. On the other hand, changes in the surface PM deposition amount lead to little changes in the saturated ammonia adsorption amount of the SCR catalyst, and little changes in the quantity of ammonia desorbed from the SCR catalyst accordingly. Therefore, it is considered that increases or decreases in the surface PM deposition amount in the SCR filter have little effect on increases or decreases in the ammonia adsorption amount in the SCR catalyst. The present disclosure applies the above-described discovery to fault diagnosis of an exhaust gas purification system that is made on the basis of the NOx removal rate with an SCR filter.

More specifically, according to a first aspect of the present disclosure, there may be provided a fault diagnosis apparatus for an exhaust gas purification system for diagnosing whether or not the exhaust gas purification system is faulty, the exhaust gas purification system including an SCR filter provided in an exhaust passage of an internal combustion engine and an ammonia supply device that supplies ammonia to said SCR filter, said SCR filter including a filter and an SCR catalyst supported on said filter, said SCR catalyst having a capability of reducing NOx in exhaust gas by using ammonia as reducing agent, and said filter having a function of trapping particulate matter in exhaust gas. The fault diagnosis apparatus may comprise: an NOx sensor provided in the exhaust passage downstream of said SCR filter; an NOx removal rate calculation unit configured to calculate the NOx removal rate with said SCR filter by using a measurement value of said NOx sensor; a determination unit configured to determine that said exhaust gas purification system is faulty, if the NOx removal rate with said SCR filter calculated by said NOx removal rate calculation unit is equal to or lower than a predetermined criterion removal rate; and a setting unit configured to set said criterion removal rate, wherein said setting unit sets the value of said criterion removal rate higher when a differential pressure change rate at a time of sensor measurement is lower than a predetermined threshold than when said differential pressure change rate is equal to or higher than said predetermined threshold, said differential pressure change rate being defined as the amount of increase in a converted differential pressure value obtained by normalizing the differential pressure of the exhaust gas across said SCR filter by the exhaust gas rate per unit increase in a filter PM deposition amount defined as the amount of particulate matter deposited in said SCR filter that is estimated on the basis of a parameter other than said converted differential pressure value, and said time of sensor measurement being defined as the time at which the measurement value of said NOx sensor used in calculation of the NOx removal rate by said NOx removal rate calculation unit is obtained.

In the exhaust gas purification system to which the present disclosure is applied, ammonia serving as reducing agent is supplied to the SCR filter by the ammonia supply device. The ammonia thus supplied is adsorbed in the SCR catalyst supported on the SCR filter. The ammonia supply device may supply ammonia in the form of either gas or liquid, or alternatively the ammonia supply device may supply precursor of ammonia.

If the NOx removal capability of the SCR filter is deteriorated due to deterioration of the SCR catalyst supported on the SCR filter or other reasons, the NOx removal rate with the SCR filter decreases. The NOx removal rate with the SCR filter decreases also in cases where the quantity of ammonia supplied to the SCR filter is smaller than a required quantity due to a trouble with the ammonia supply device. Therefore, in the context of the present disclosure, faults of the exhaust gas purification system include not only deterioration of the NOx removal capability of the SCR filter but also abnormality of the ammonia supply device.

In the apparatus according to the present disclosure, the NOx removal rate calculation unit may calculate the NOx removal rate with the SCR filter by using a measurement value of the NOx sensor provided in the exhaust passage downstream of the SCR filter. If the NOx removal rate with the SCR filter is equal to or lower than a predetermined criterion removal rate, the determination unit may determine that the exhaust gas purification system is faulty. The criterion removal rate mentioned above may be set as a threshold value of the NOx removal rate with the SCR filter at or below which a determination that the exhaust gas purification system is faulty is to be made.

According to the above-described discovery made by the inventors, even if the NOx removal capability of the SCR filter is in the same condition and the quantity of ammonia supplied to the SCR filter is the same, the quantity of ammonia adsorbed in the SCR catalyst may vary depending on the state of deposition of PM in the SCR filter. More specifically, as described above, the mode of deposition of PM in the SCR filter shifts to surface PM deposition after the in-wall PM deposition amount reaches its upper limit. Therefore, during the surface PM deposition period, the in-wall PM deposition amount is always at its upper limit. This means that during the surface PM deposition period, the in-wall PM deposition amount is larger than that during the in-wall PM deposition period. The ammonia adsorption amount in the SCR catalyst is more apt to increase when the in-wall PM deposition amount is large than when the in-wall PM deposition amount is small. Therefore, even if the NOx removal capability of the SCR filter is in the same condition and the quantity of ammonia supplied to the SCR filter is the same, the ammonia adsorption amount in the SCR catalyst is larger during the surface PM deposition period than during the in-wall PM deposition period.

The larger the ammonia adsorption amount in the SCR catalyst is, the larger the quantity of NOx reduced in the SCR catalyst is. Therefore, if the values of the parameters relating to the NOx removal rate other than the ammonia adsorption amount in the SCR catalyst are the same, the larger the ammonia adsorption amount in the SCR catalyst is, the higher the NOx removal rate is. Therefore, even if the NOx removal capability of the SCR filter is in the same condition and the quantity of ammonia supplied to the SCR filter is the same, the value of the NOx removal rate calculated by the NOX removal rate calculation unit is higher during the surface PM deposition period than during the in-wall PM deposition period.

Therefore, if the criterion removal rate serving as the threshold for determination of a fault of the exhaust gas purification system is set without taking account of whether the time of sensor measurement is during the surface PM deposition period or the in-wall PM deposition period, a wrong determination in fault diagnosis can be made. To address this problem, according to the present disclosure, the setting unit may be configured to set the criterion removal rate at different values depending on whether the time of sensor measurement is during the surface PM deposition period or the in-wall PM deposition period. The time of sensor measurement may refer to the time at which the measurement value of the NOx sensor used in calculation of the NOx removal rate with the SCR filter is obtained.

Specifically, the setting unit may set the value of the criterion removal rate higher when the differential pressure change rate at the time of sensor measurement is lower than a predetermined threshold than when the differential pressure change rate at the time of sensor measurement is equal to or higher than the predetermined threshold. The differential pressure change rate mentioned above may be the amount of increase in the converted differential pressure value per unit increase in the filter PM deposition amount.

The value of the PM deposition amount may be estimated on the basis of a parameter other than the converted differential pressure value. The value of the differential pressure change rate defined as above is lower during the surface PM deposition period than during the in-wall PM deposition period. Therefore, the predetermined threshold referred to in the apparatus according to the present disclosure may be set to a value with which a distinction between whether it is during the in-wall PM deposition period or during the surface PM deposition period now can be made, namely a value with which an identification between the in-wall PM deposition period and the surface PM deposition period can be made.

The mode of PM deposition in the SCR filter shifts to surface PM deposition after in-wall PM deposition reaches its upper limit. However, it should be noted that oxidation of PM in the SCR filter can occur both in partition walls of the SCR filter and on the surface of partition walls. Therefore, even after the mode of PM deposition in the SCR filter has once shifted to surface PM deposition, the in-wall PM deposition amount may be decreased by oxidation of PM in partition walls in some cases. In such cases, when deposition of PM restarts, PM is deposited in partition walls again, in other words, the mode of deposition shifts from surface PM deposition to in-wall PM deposition. Hence, it is difficult to make an identification between the in-wall PM deposition period and the surface PM deposition period accurately only on the basis of the time elapsed since the start of deposition of PM in the SCR filter or the filter PM deposition amount (i.e. the overall amount of PM deposited in the SCR filter). Therefore, in the apparatus according to the present disclosure, the differential pressure change rate may be used as a parameter to make an identification between the in-wall PM deposition period and the surface PM deposition period.

With the above-described way of setting the criterion removal rate, the value of the criterion removal rate is set higher in the case where the time of sensor measurement is during the surface PM deposition period than in the case where the time of sensor measurement is during the in-wall PM deposition period. Thus, even though the value of the NOx removal rate calculated by the NOx removal rate calculation unit is a value affected by the state of deposition of PM in the SCR filter, the criterion removal rate to be compared with the NOx removal rate in fault diagnosis is set to a more appropriate value. Therefore, the present disclosure can improve the accuracy of fault diagnosis of the exhaust gas purification system having the SCR filter.

According to the above-described discovery, increases or decreases in the surface PM deposition amount in the SCR filter have little effect on increases or decreases in the ammonia adsorption amount in the SCR catalyst. Therefore, increases or decreases in the surface PM deposition amount in the SCR filter have little effect on the NOx removal rate with the SCR filter. In view of this, in the apparatus according to the present disclosure, in the case where the differential pressure change rate at the time of sensor measurement is lower than the predetermined threshold, a change in the criterion removal rate set by the setting unit relative to a change in the filter PM deposition amount at the time of sensor measurement may be made equal zero. Thus, in the case where the time of sensor measurement is during the surface PM deposition period, the filter PM deposition amount at the time of sensor measurement does not affect the setting of the criterion removal rate. Therefore, the accuracy of fault diagnosis of the exhaust gas purification system in the case where the time of sensor measurement is during the surface PM deposition period can further be improved.

The lower the temperature of the SCR filter is, the larger the magnitude of increase in the ammonia adsorption amount in the SCR catalyst attributable to deposition of PM in partition walls of the SCR filter is. Therefore, during the surface PM deposition period, the lower the temperature of the SCR filter is, the higher the NOx removal rate is, if the values of the parameters relating to the NOx removal rate other than the temperature of the SCR filter are the same. In view of this, in the apparatus according to the present disclosure, in setting the value of the criterion removal rate higher in the case where the differential pressure change rate at the time of sensor measurement is lower than the predetermined threshold than in the case where the differential pressure change rate at the time of sensor measurement is equal to or higher than the predetermined threshold, the setting unit may set the value of the criterion removal rate higher when the temperature of the SCR filter at the time of sensor measurement is low than when the temperature of the SCR filter at the time of sensor measurement is high. Thus, in the case where the time of sensor measurement is during the surface PM deposition period, the value of the criterion removal rate is set higher when the temperature of the SCR filter at the time of sensor measurement is low than when the temperature of the SCR filter at the time of sensor measurement is high. Therefore, the accuracy of fault diagnosis of the exhaust gas purification system in the case where the time of sensor measurement is during the surface PM deposition period can further be improved.

According to a second aspect of the present disclosure, there may be provided a fault diagnosis apparatus for an exhaust gas purification system for diagnosing whether or not the exhaust gas purification system is faulty, the exhaust gas purification system including an SCR filter provided in an exhaust passage of an internal combustion engine and an ammonia supply device that supplies ammonia to said SCR filter, said SCR filter including a filter and an SCR catalyst supported on said filter, said SCR catalyst having a capability of reducing NOx in exhaust gas by using ammonia as reducing agent, and said filter having a function of trapping particulate matter in exhaust gas. The fault diagnosis apparatus may comprise: an NOx sensor provided in the exhaust passage downstream of said SCR filter; an NOx removal rate calculation unit configured to calculate the NOx removal rate with said SCR filter by using a measurement value of said NOx sensor; a corrected removal rate calculation unit configured to calculate a corrected removal rate by subtracting a decrease that is determined on the basis of a differential pressure change rate at a time of sensor measurement from the NOx removal rate with said SCR filter calculated by said NOx removal rate calculation unit, said differential pressure change rate being defined as the amount of increase in a converted differential pressure value obtained by normalizing the differential pressure of the exhaust gas across said SCR filter by the exhaust gas rate per unit increase in a filter PM deposition amount defined as the amount of particulate matter deposited in said SCR filter that is estimated on the basis of a parameter other than said converted differential pressure value, and said time of sensor measurement being defined as the time at which the measurement value of said NOx sensor used in calculation of the NOx removal rate by said NOx removal rate calculation unit is obtained; and a determination unit configured to determine that said exhaust gas purification system is faulty, if said corrected removal rate calculated by said corrected removal rate calculation unit is equal to or lower than a predetermined criterion removal rate that is determined on the assumption that particulate matter is not deposited in said SCR filter, wherein said corrected removal rate calculation unit makes said decrease larger in the case where said differential pressure change rate at said time of sensor measurement is lower than a predetermined threshold than in the case where said differential pressure change rate at said time of sensor measurement is equal to or higher than said predetermined threshold.

In the apparatus according to the second aspect of the present disclosure, the criterion removal rate may be set as a criterion removal rate in the case where it is assumed that PM is not deposited in the SCR filter. In other words, the criterion removal rate set in the apparatus according the second aspect of the present disclosure may be a value set as a threshold value of the NOx removal rate with the SCR filter in the state in which PM is not deposited therein below which a determination that the exhaust gas purification system is faulty is to be made. In the apparatus according to the second aspect of the present disclosure, a corrected removal rate may be calculated by subtracting a certain decrease that is determined on the basis of the differential pressure change rate at the time of sensor measurement from the NOx removal rate calculated by the NOx removal rate calculation unit. Then, the corrected removal rate and the criterion removal rate may be compared to determine whether or not the exhaust gas purification system is faulty.

As described above, even if the NOx removal capability of the SCR filter is in the same condition and the quantity of ammonia supplied to the SCR filter is the same, the value of the NOx removal rate calculated by the NOX removal rate calculation unit is higher during the surface PM deposition period than during the in-wall PM deposition period. Therefore, in the apparatus according to the second aspect of the present disclosure, in the case where the differential pressure change rate at the time of sensor measurement is lower than the predetermined threshold, namely in the case where the time of sensor measurement is during the surface PM deposition period, the decrease that is subtracted from the value of the NOx removal rate calculated by the NOx removal rate calculation unit in calculation of the corrected removal rate may be made larger than that in the case where the differential pressure change rate is equal to or higher than the predetermined threshold, namely that in the case where the time of sensor measurement is during the in-wall PM deposition period. Thus, even when the value of the NOx removal rate with the SCR catalyst calculated by the NOx removal rate calculation unit is a value affected by the state of deposition of PM in the SCR filter, the corrected removal rate to be compared with the criterion removal rate in fault diagnosis is set to a more appropriate value. Therefore, the second aspect of the present disclosure can improve the accuracy of fault diagnosis of the exhaust gas purification system having the SCR filter, as with the first aspect of the present disclosure.

In the apparatus according to the second aspect of the present disclosure, in the case where the differential pressure change rate at the time of sensor measurement is lower than the predetermined threshold, namely in the case where the time of sensor measurement is during the surface PM deposition period, a change in the decrease to be subtracted from the NOx removal rate calculated by the NOx removal rate calculation unit may be made equal to zero. In other words, the intact value of the NOx removal rate calculated by the NOx removal rate calculation unit may be used as the corrected removal rate.

In the apparatus according to the second aspect of the present disclosure, in the case where the differential pressure change rate at the time of sensor measurement is lower than the predetermined threshold, the change in the decrease to be subtracted from the NOx removal rate calculated by the NOx removal rate calculation unit in calculation of the corrected removal rate by the corrected removal rate calculation unit relative to the change in said filter PM deposition amount at said time of sensor measurement may be made equal to zero. Thus, in the case where the time of sensor measurement is during the surface PM deposition period, the filter PM deposition amount at the time of sensor measurement does not affect the calculation of the corrected removal rate. Therefore, the accuracy of fault diagnosis of the exhaust gas purification system in the case where the time of sensor measurement is during the surface PM deposition period can further be improved.

In the apparatus according to the second aspect of the present disclosure, in the case where the differential pressure change rate at the time of sensor measurement is lower than the predetermined threshold, the corrected removal rate calculation unit makes the decrease to be subtracted from the value of the NOx removal rate calculated by the NOx removal rate calculation unit in calculation of the corrected removal rate larger than that in the case where the differential pressure change rate is equal to or higher than the predetermined threshold. In doing so, the corrected removal rate calculation unit may make the aforementioned decrease larger when the temperature of the SCR filter at the time of sensor measurement is low than when the temperature of the SCR filter at the time of sensor measurement is high. Thus, even when the value of the NOx removal rate calculated by the NOx removal rate calculation unit is a value affected by the state of deposition of PM in the SCR filter, the corrected removal rate to be compared with the criterion removal rate in fault diagnosis is set to a more appropriate value. Therefore, the accuracy of fault diagnosis of the exhaust gas purification system in the case where the time of sensor measurement is during the surface PM deposition period can further be improved.

The present disclosure can improve the accuracy of diagnosis as to whether or not an exhaust gas purification system equipped with an SCR filter is faulty.

DESCRIPTION OF EMBODIMENTS

In the following, a specific embodiment of the present disclosure will be described with reference to the drawings. The dimensions, materials, shapes, relative arrangements, and other features of the components that will be described in connection with the embodiment are not intended to limit the technical scope of the present disclosure only to them, unless particularly stated.

Embodiment 1

Figure 1:
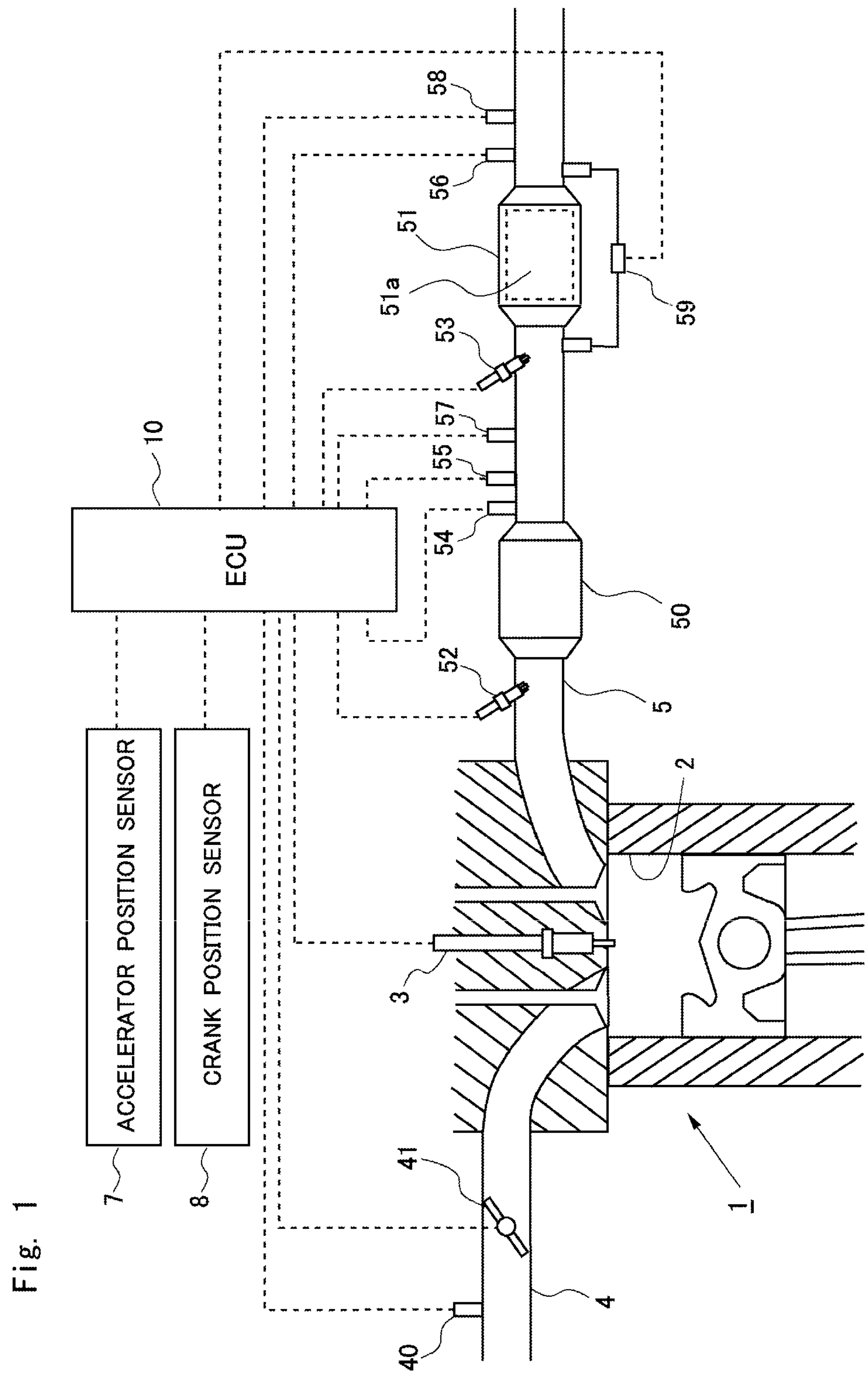
FIG. 1 is a diagram showing the general configuration of an internal combustion engine and its air-intake and exhaust systems according to embodiments of the present disclosure.

FIG. 1 is a diagram showing the general configuration of an internal combustion engine and its air-intake and exhaust systems according to a first embodiment. The internal combustion engine 1 shown in FIG. 1 is a compression-ignition internal combustion engine (diesel engine) using light oil as fuel. It should be understood that the present disclosure can also be applied to a spark-ignition internal combustion engine using gasoline or the like as fuel.

The internal combustion engine 1 has a fuel injection valve 3 that injects fuel into a cylinder 2. In the case where the internal combustion engine 1 is a spark-ignition internal combustion engine, the fuel injection valve 3 may be adapted to inject fuel into an intake port.

The internal combustion engine 1 is connected with an intake passage 4. The intake passage 4 is provided with an air flow meter 40 and a throttle valve 41. The air flow meter 40 outputs an electrical signal representing the quantity (or mass) of the intake air flowing in the intake passage 4. The throttle valve 41 is arranged in the intake passage 4 downstream of the air-flow meter 40. The throttle valve 41 changes the channel cross sectional area of the intake passage 4 to adjust the intake air quantity of the internal combustion engine 1.

The internal combustion engine 1 is connected with an exhaust passage 5. The exhaust passage 5 is provided with an oxidation catalyst 50, an SCR filter 51, a fuel addition valve 52, and a urea solution addition valve 53. The SCR filter 51 is composed of a wall-flow filter made of a porous base material and an SCR catalyst 51*a* supported thereon. The filter has the function of trapping PM in the exhaust gas. The SCR catalyst 51*a* is capable of reducing NOx in the exhaust gas using ammonia as reducing agent. Thus, the SCR filter 51 is capable of trapping PM and removing NOx. The oxidation catalyst 50 is arranged in the exhaust passage 5 upstream of the SCR filter 51. The fuel addition valve 52 is arranged in the exhaust passage 5 upstream of the oxidation catalyst 50. The fuel addition valve 52 is used to add fuel to the exhaust gas flowing in the exhaust passage 5. The urea solution addition valve 53 is arranged in the exhaust passage 5 downstream of the oxidation catalyst 50 and upstream of the SCR filter 51. The urea solution addition valve 53 is used to add urea solution to the exhaust gas flowing in the exhaust passage 5. As urea solution is added to the exhaust gas through the urea solution addition valve 53, the urea solution is supplied to the SCR filter 51. Thus, urea as a precursor of ammonia is supplied to the SCR filter 51. In the SCR filter 51, ammonia generated by hydrolysis of supplied urea is adsorbed in the SCR catalyst 51*a*. The ammonia adsorbed in the SCR catalyst 51*a* functions as a reducing agent to reduce NOx in the exhaust gas. The urea solution addition valve 53 may be replaced by an ammonia addition valve that adds ammonia gas to the exhaust gas.

The exhaust passage 5 downstream of the oxidation catalyst 50 and upstream of the urea solution addition valve 53 is provided with an $O_2$ sensor 54, an upstream temperature sensor 55, and an upstream NOx sensor 57. The exhaust passage 5 downstream of the SCR filter 51 is provided with a downstream temperature sensor 56 and a downstream NOx sensor 58. The $O_2$ sensor 54 outputs an electrical signal representing the $O_2$ concentration in the exhaust gas. The upstream temperature sensor 55 and the downstream temperature sensor 56 each output an electrical signal representing the temperature of the exhaust gas. The upstream NOx sensor 57 and the downstream NOx sensor 58 each output an electrical signal representing the NOx concentration in the exhaust gas. The exhaust passage 5 is provided with a differential pressure sensor 59. The differential pressure sensor 59 outputs an electrical signal representing the differential pressure of exhaust gas across the SCR filter 51, which will be sometimes referred to as the filter differential pressure hereinafter.

The internal combustion engine 1 is equipped with an electronic control unit (ECU) 10. The ECU 10 is a unit that controls the operation state of the internal combustion engine 1. The ECU 10 is electrically connected with various sensors including an accelerator position sensor 7 and a crank position sensor 8 as well as the air flow meter 40, the $O_2$ sensor 54, the upstream temperature sensor 55, the upstream NOx sensor 57, the downstream temperature sensor 56, the downstream NOx sensor 58, and the differential pressure sensor 59 mentioned above. The accelerator position sensor 7 is a sensor that outputs an electrical signal representing the amount of operation of an accelerator pedal (accelerator opening degree), which is not shown in the drawings. The crank position sensor 8 is a sensor that outputs an electrical signal representing the rotational position of the engine output shaft (or crankshaft) of the internal combustion engine 1. Signals output from these sensors are input to the ECU 10. The ECU 10 estimates the temperature of the SCR filter 51 on the basis of the output value of the downstream temperature sensor 56. This temperature will be sometimes referred to as the “filter temperature” hereinafter. The ECU 10 estimates the flow rate of the exhaust gas flowing into the SCR filter 51 on the basis of the output value of the air flow meter 40. This flow rate will be sometimes simply referred to as the “exhaust gas flow rate” hereinafter.

The ECU 10 is electrically connected with various devices including the fuel injection valve 3, the throttle valve 41, the fuel addition valve 52, and the urea solution addition valve 53 mentioned above. The ECU 10 controls these devices using signals output from the aforementioned sensors. For instance, the ECU 10 controls the quantity of urea solution added through the urea solution addition valve 53 so as to keep/adjust the ammonia adsorption amount in the SCR catalyst 51*a* at/to a predetermined target adsorption amount. The predetermined target adsorption amount is determined in advance by, for example, an experiment as a value at which a desired NOx removal rate with the SCR filter 51 can be achieved and the quantity of ammonia flowing out of the SCR filter 51 can be kept within an allowable range.

The ECU 10 executes a filter regeneration process by adding fuel through the fuel addition valve 52 when the amount of PM deposited in the SCR filter 51 (which will be sometimes referred to as the "filter PM deposition amount" hereinafter) reaches a predetermined deposition amount. The filter PM deposition amount is estimated by a method that will be described later. In the filter regeneration process, the temperature of the SCR filter 51 is raised by oxidation heat produced by oxidation of fuel added through the fuel addition valve 52 in the oxidation catalyst 50. As a result, the PM deposited in the SCR filter 51 is burned and removed.

(Estimation of the Filter PM Deposition Amount)

Figure 2:
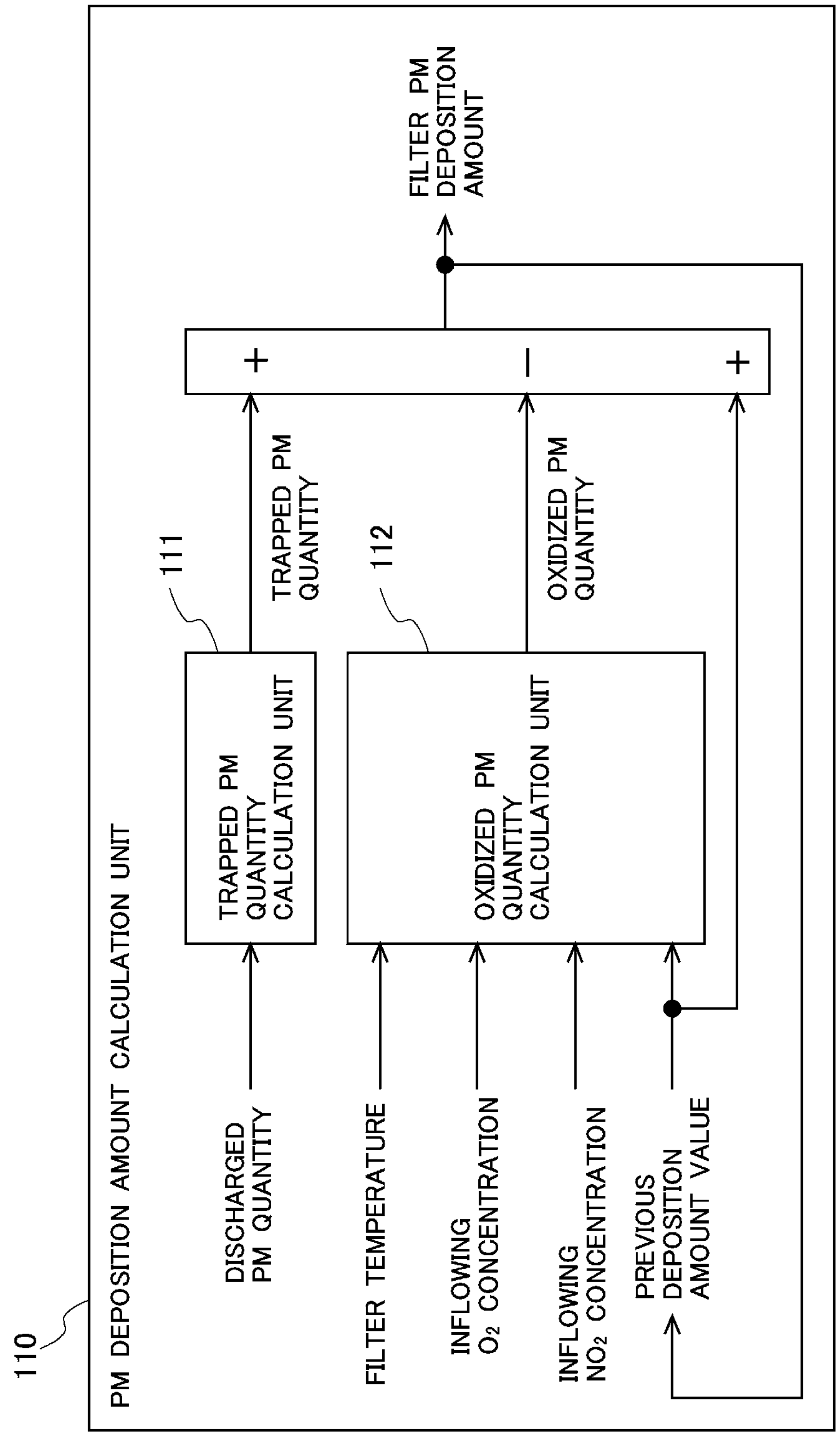
FIG. 2 is a block diagram illustrating the functions of a PM deposition amount calculation unit in an ECU according to the embodiments of the present disclosure.

In this embodiment, the ECU 10 calculates the filter PM deposition amount repeatedly at regular calculation intervals. FIG. 2 is a block diagram illustrating the functions of a PM deposition amount calculation unit in the ECU 10. The PM deposition amount calculation unit 110 is a functional unit configured to calculate the filter PM deposition amount. The PM deposition amount calculation unit 110 is constituted by execution of a certain program in the ECU 10. The PM deposition amount calculation unit 110 in this embodiment is configured to calculate the filter PM deposition amount without using a converted differential pressure value, which is obtained by normalizing the filter differential pressure measured by the differential pressure sensor 59 by the exhaust gas flow rate. The converted differential pressure value will be described later. Furthermore, the PM deposition amount calculation unit 110 in this embodiment is configured to calculate the filter PM deposition amount on the assumption that the PM trapping function of the SCR filter 51 is in a normal condition.

The PM deposition amount calculation unit 110 calculates the filter PM deposition amount at the present time by integrating the trapped PM quantity defined as the quantity of PM trapped by the SCR filter 51 and the oxidized PM quantity defined as the quantity of PM oxidized in the SCR filter 51. Specifically, the PM deposition amount calculation unit 110 includes a trapped PM quantity calculation unit 111 and an oxidized PM quantity calculation unit 112. The trapped PM quantity calculation unit 111 calculates a trapped PM quantity as the quantity of PM trapped by the SCR filter 51 over a first predetermined period that is determined in accordance with the interval of calculation of the filter PM deposition amount. The oxidized PM quantity calculation unit 112 calculates an oxidized PM quantity as the quantity of PM oxidized in the SCR filter 51 over the first predetermined period.

The trapped PM quantity calculation unit 111 has as an input the quantity of PM discharged from the internal combustion engine 1 over the first predetermined period (which will be sometimes simply referred to as the "discharged PM quantity" hereinafter). The discharged PM quantity can be estimated on the basis of the operation state of the internal combustion engine 1. The trapped PM quantity calculation unit 111 calculates the trapped PM quantity by multiplying the input value of the discharged PM quantity by a predetermined PM trapping rate, which is the rate of the quantity of PM trapped by the SCR filter 51 to the quantity of PM flowing into the SCR filter 51. The predetermined PM trapping rate may be a value estimated on the basis of the exhaust gas flow rate.

The oxidized PM quantity calculation unit 112 has as inputs the filter temperature, the $O_2$ concentration in the exhaust gas flowing into the SCR filter 51 (which will be sometimes referred to as the "inflowing $O_2$ concentration" hereinafter), and the $NO_2$ concentration in the exhaust gas flowing into the SCR filter 51 (which will be sometimes referred to as the "inflowing $NO_2$ concentration" hereinafter). The filter temperature can be estimated from the output value of the downstream temperature sensor 56. The inflowing $O_2$ concentration is measured by the $O_2$ sensor 54. Alternatively, the inflowing $O_2$ concentration can be estimated on the basis of the air-fuel ratio of the exhaust gas and the operation state of the internal combustion engine 1 etc. The inflowing $NO_2$ concentration can be estimated from the output value of the air flow meter 40, the output value of the upstream temperature sensor 55, and the output value of the upstream NOx sensor 57 etc. More specifically, the quantity of NOx in the exhaust gas can be estimated from the output value of the upstream NOx sensor 57 and the exhaust gas flow rate. The proportion of the quantity of $NO_2$ in the quantity of NOx in the exhaust gas can be estimated from the temperature of the oxidation catalyst 50, which is estimated from the output value of the upstream temperature sensor 55, and the exhaust gas flow rate. Then, the inflowing $NO_2$ concentration can be estimated from the quantity of NOx in the exhaust gas and the estimated proportion of the quantity of $NO_2$ in the quantity of NOx in the exhaust gas etc. Furthermore, the oxidized PM quantity calculation unit 112 also has as an input a value of the filter PM deposition amount calculated in the previous (or last time) calculation. This input value will be sometimes referred to as the "previous deposition amount value" hereinafter. The oxidized PM quantity calculation unit 112 calculates the oxidized PM quantity from the input values of the filter temperature, the inflowing $O_2$ concentration, the inflowing $NO_2$ concentration, and the previous deposition amount value.

The PM deposition amount calculation unit 110 calculates the filter PM deposition amount of this time (or the filter PM deposition amount at the present time) by adding the trapped PM quantity as an increase to the previous deposition amount value and subtracting the oxidized PM quantity as a decrease from it. The filter PM deposition amount of this time thus calculated will serve as the previous deposition amount value in the next time calculation process.

The method of calculation of the filter PM deposition amount according to the present disclosure is not limited to that described above. In the present disclosure, the filter PM deposition amount may be calculated by any known method without using the converted differential pressure value that will be described later.

(Estimation of Ammonia Adsorption Amount)

Figure 3:
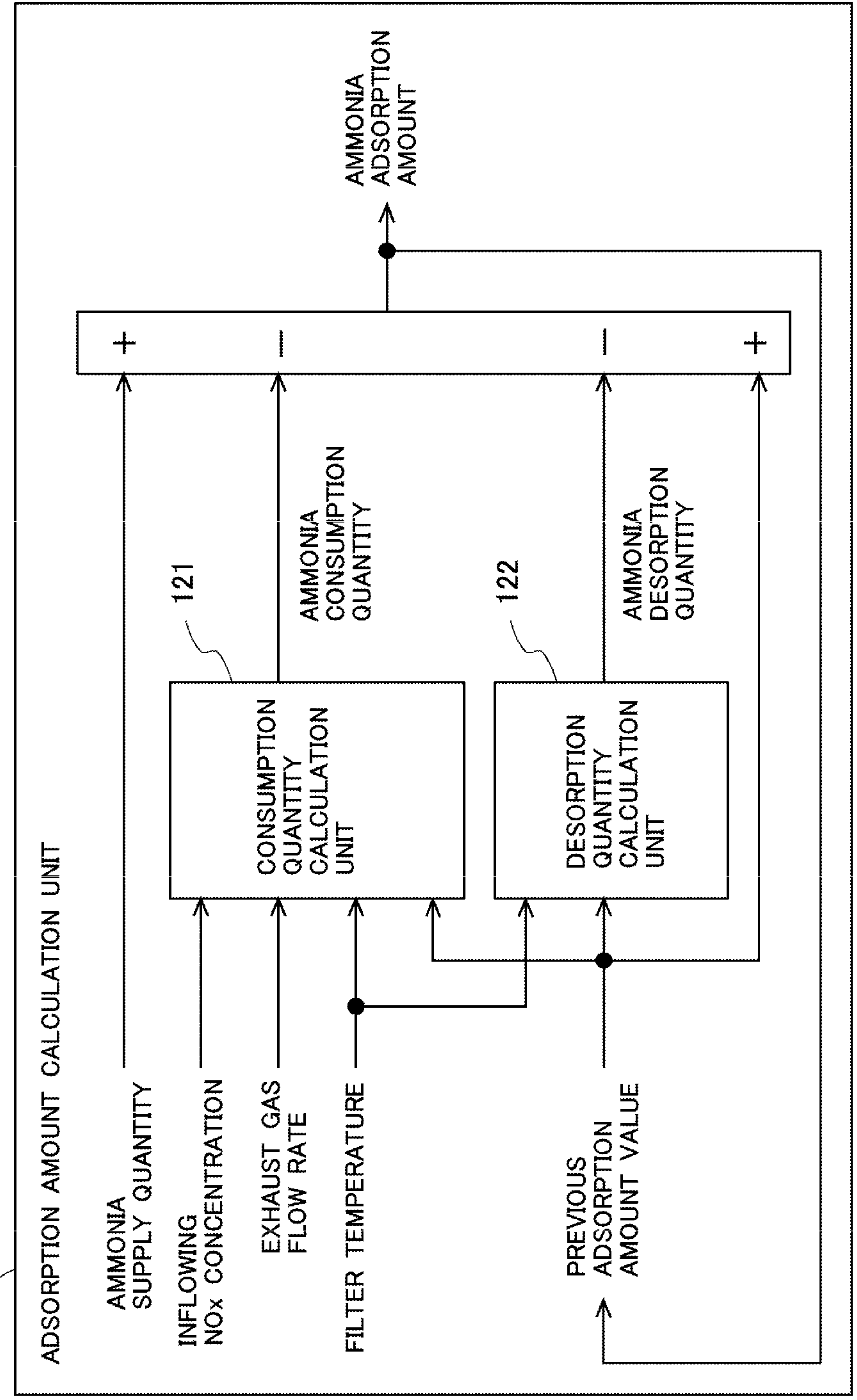
FIG. 3 is a block diagram illustrating the functions of an adsorption amount calculation unit in the ECU according to the embodiments of the present disclosure.

In this embodiment, the ECU 10 calculates the ammonia adsorption amount defined as the amount of ammonia adsorbed in the SCR catalyst 51*a* repeatedly at a predetermined calculation interval. FIG. 3 is a block diagram illustrating the functions of an adsorption amount calculation unit in the ECU 10. The adsorption amount calculation unit 120 is a functional unit configured to calculate the amount of ammonia adsorbed in the SCR catalyst 51*a*. The adsorption amount calculation unit 120 is constituted by execution of a certain program in the ECU 10. The adsorption amount calculation unit 120 in this embodiment is configured to calculate the ammonia adsorption amount on the assumption that the NOx removal capability of the SCR filter 51 is in a normal condition. Moreover, the adsorption amount calculation unit 120 in this embodiment is configured to calculate the ammonia adsorption amount on the assumption that PM is not deposited in the SCR filter 51. Therefore, in the value of the ammonia adsorption amount calculated by the adsorption amount calculation unit 120, the influence of the state of deposition of PM in the SCR filter 51 on the ammonia adsorption amount in the SCR catalyst 51*a* is not taken into account. The influence of the state of deposition of PM in the SCR filter 51 on the ammonia adsorption amount in the SCR catalyst 51*a* will be described later.

The adsorption amount calculation unit 120 calculates the ammonia adsorption amount at the present time by integrating the ammonia supply quantity defined as the quantity of ammonia supplied to the SCR filter 51, the ammonia consumption quantity defined as the quantity of ammonia consumed in reduction of NOx in the SCR catalyst 51*a*, and the ammonia desorption quantity defined as the quantity of ammonia desorbed from the SCR catalyst 51*a*. Specifically, the adsorption amount calculation unit 120 includes a consumption quantity calculation unit 121 and a desorption quantity calculation unit 122. The consumption quantity calculation unit 121 calculates the ammonia consumption quantity as the quantity of ammonia consumed in reduction of NOx in the SCR catalyst 51*a* over a second predetermined period that is determined in accordance with the interval of calculation of the ammonia adsorption amount. The desorption quantity calculation unit 122 calculates the ammonia desorption quantity as the quantity of ammonia desorbed from the SCR catalyst 51*a* over the second predetermined period. Furthermore, the adsorption amount calculation unit 120 is configured to estimate the ammonia supply quantity as the quantity of ammonia supplied to the SCR filter 51 over the second predetermined period. As described above, the ammonia supplied to the SCR filter 51 is produced by hydrolysis of urea contained in urea solution added through the urea solution addition valve 53. Therefore, the ammonia supply quantity can be estimated from the quantity of urea solution added through the urea solution addition valve 53 over the second predetermined period.

The consumption quantity calculation unit 121 has as inputs the NOx concentration in the exhaust gas flowing into the SCR filter 51 (which will be sometimes referred to as the "inflowing NOx concentration" hereinafter), the exhaust gas flow rate, the filter temperature, and the value of the ammonia adsorption amount in the SCR catalyst 51*a* calculated in the previous (or last time) calculation (which will be sometimes referred to as the "previous adsorption amount value" hereinafter). The inflowing NOx concentration is measured by the upstream NOx sensor 57. The NOx removal rate with the SCR catalyst 51*a* depends on the exhaust gas flow rate, the filter temperature, and the ammonia adsorption amount in the SCR catalyst 51*a*. Therefore, the consumption quantity calculation unit 121 is configured to calculate the NOx removal rate expected to be achieved by the SCR catalyst 51*a* at the present time (which will be hereinafter referred to as the "estimated NOx removal rate") from the input values of the exhaust gas flow rate, the filter temperature, and the previous adsorption amount value. Furthermore, the consumption quantity calculation unit 121 is also configured to calculate the quantity of NOx flowing into the SCR filter 51 over the second predetermined period (which will be sometimes referred to as the "inflowing NOx quantity" hereinafter) from the input values of the inflowing NOx concentration and the exhaust gas flow rate. The ammonia consumption quantity is calculated from the estimated NOx removal rate and the inflowing NOx quantity calculated as above.

The desorption quantity calculation unit 122 has as inputs the filter temperature and the previous adsorption amount value. If the ammonia adsorption amount in the SCR catalyst 51*a* is the same, the higher the filter temperature is, the larger the ammonia desorption quantity is. If the filter temperature is the same, the larger the ammonia adsorption amount in the SCR catalyst 51*a* is, the larger the ammonia desorption quantity is. The desorption quantity calculation unit 122 calculates the ammonia desorption quantity from the input values of the filter temperature and the previous adsorption amount value on the basis of the above relationships.

The adsorption amount calculation unit 120 is configured to calculate the value of the ammonia adsorption amount in the SCR catalyst 51*a* of this time by adding the ammonia supply quantity as an increase to the previous adsorption amount value and subtracting the ammonia consumption quantity and the ammonia desorption quantity as decreases from it.

(Relationship Between State of Deposition of PM and Ammonia Adsorption Amount)

Now, we will discuss relationship between the state of deposition of PM in the SCR filter 51 and the ammonia adsorption amount in the SCR catalyst 51*a*. As described before, the inventors of the present disclosure made findings about relationship between the state of deposition of PM in the SCR filter and the tendency of increase of the ammonia adsorption amount in the SCR catalyst. According to the findings, when the filter temperature and the ammonia adsorption amount in the SCR catalyst 51*a* are the same, the ammonia desorption quantity is smaller when the amount of PM deposited in the partition walls of the SCR filter 51 (or the in-wall PM deposition amount) is large than when the in-wall PM deposition amount is small. Therefore, when the values of the other parameters relating to the increase of the ammonia adsorption amount in the SCR catalyst 51*a* remain the same, the ammonia adsorption amount in the SCR catalyst 51*a* is more apt to increase when the in-wall PM deposition amount is large than when the in-wall PM deposition amount is small. At times after the in-wall PM deposition amount in the SCR filter 51 has reached its upper limit and the mode of deposition of PM in the SCR filter 51 has shifted from in-wall PM deposition to surface PM deposition, the ammonia desorption quantity changes little even when the filter PM deposition amount (that is, the surface PM deposition amount) changes, so long as the filter temperature and the ammonia adsorption amount in the SCR catalyst 51*a* remain the same. Therefore, increases or decreases in the surface PM deposition amount have little effect on increases or decreases in the ammonia adsorption amount in the SCR catalyst 51*a*.

Figure 4:
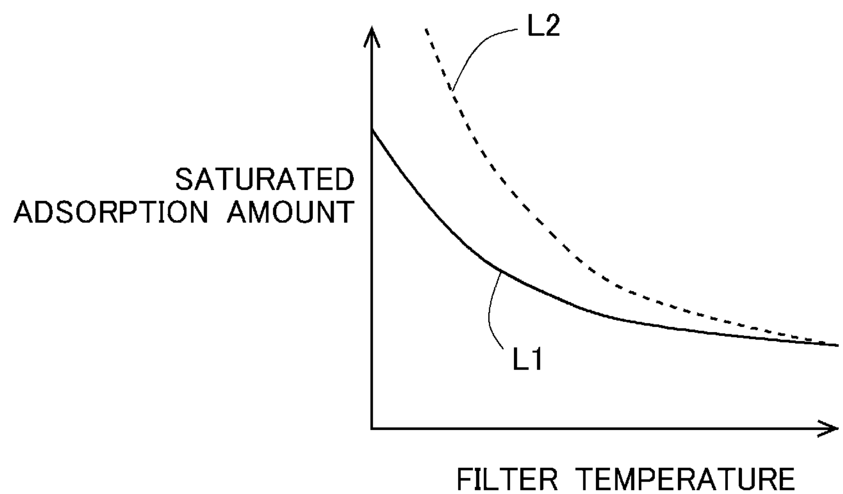
FIG. 4 is a graph showing how the state of deposition of PM in an SCR filter affects the saturated ammonia adsorption amount of an SCR catalyst supported on the SCR filter.

The above-described tendency of change in the ammonia adsorption amount in the SCR catalyst 51*a* depending on the state of deposition of PM in the SCR filter 51 is considered to be attributable to relation between the state of deposition of PM in the SCR filter 51 and the saturated ammonia adsorption amount in the SCR catalyst 51*a*. The saturated ammonia adsorption amount is the largest amount of ammonia that can be adsorbed in the SCR catalyst 51*a*, which will be sometimes simply referred to as the "saturated adsorption amount" hereinafter. FIG. 4 is a graph illustrating how the state of deposition of PM in the SCR filter 51 affects the saturated adsorption amount of the SCR catalyst 51*a*. In FIG. 4, the horizontal axis represents the filter temperature, and the vertical axis represents the saturated adsorption amount of the SCR catalyst 51*a*. Line L1 in FIG. 4 represents relationship between the filter temperature and the saturated adsorption amount in a state in which PM is not deposited in the SCR filter 51. Line L2 in FIG. 4 represents relationship between the filter temperature and the saturated adsorption amount in a state in which PM is deposited in the SCR filter 51. The higher the filter temperature is (namely, the higher the temperature of the SCR catalyst 51*a* is), the more ammonia is apt to be desorbed from the SCR catalyst 51*a*. Therefore, the higher the filter temperature is, the smaller the saturated adsorption amount of the SCR catalyst 51*a* is. Equivalently, the lower the filter temperature is, the larger the saturated adsorption amount of the SCR catalyst 51*a* is. As shown in FIG. 4, at the same filter temperature, the saturated adsorption amount of the SCR catalyst 51*a* is larger in the state in which PM is deposited in the SCR filter 51 than in the state in which PM is not deposited in the SCR filter 51.

Figure 5:
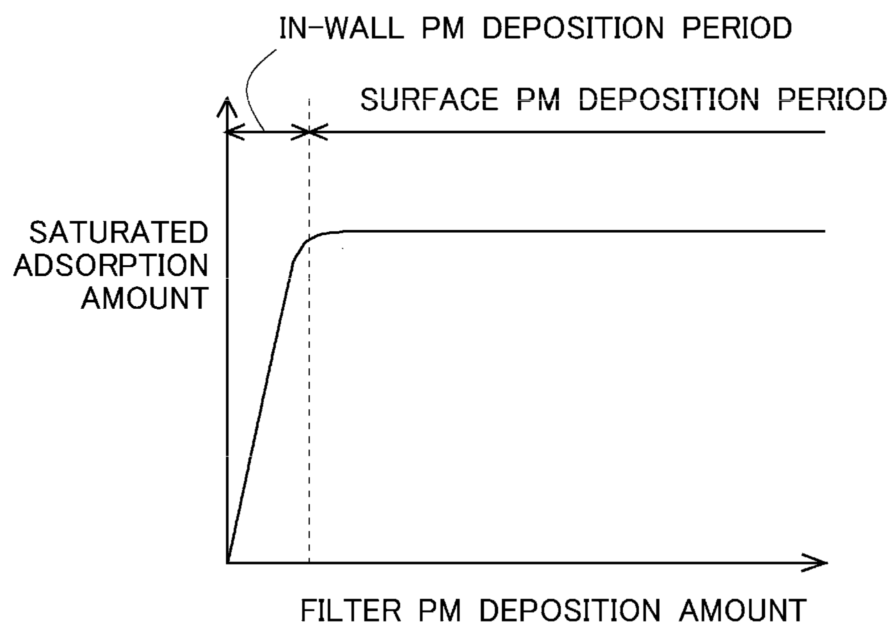
FIG. 5 is a graph showing relationship between the state of deposition of PM in the SCR filter and the saturated ammonia adsorption amount of the SCR catalyst.

Relationship between the state of deposition of PM in the SCR filter 51 and the saturated adsorption amount of the SCR catalyst 51*a* will be described below more specifically with reference to FIG. 5. FIG. 5 is a graph showing relationship between the state of deposition of PM in the SCR filter 51 and the saturated adsorption amount of the SCR catalyst 51*a*. In FIG. 5, the horizontal axis represents the filter PM deposition amount, and the vertical axis represents the saturated adsorption amount of the SCR catalyst 51*a*. FIG. 5 shows the change of the saturated adsorption amount of the SCR catalyst 51*a* in a case where the filter temperature is kept constant.

As shown in FIG. 5, in the process of deposition of PM in the SCR filter 51, PM firstly deposits in partition walls (specifically, micro-pores in partition walls). Then, after the in-wall PM deposition amount reaches its upper limit, PM deposits on the surface of partition walls. In other words, after the upper limit of the in-wall PM deposition amount is reached, the mode of deposition of PM in the SCR filter 51 shifts from in-wall PM deposition to surface PM deposition. In this process, as shown in FIG. 5, during the in-wall PM deposition period, the saturated adsorption amount of the SCR catalyst 51*a* increases in accordance with the increase in the filter PM deposition amount, namely in accordance with the increase in the in-wall PM deposition amount. On the other hand, during the surface PM deposition period, the saturated adsorption amount of the SCR catalyst 51*a* does not increase, even while the filter PM deposition amount increases, namely even while the surface PM deposition amount increases. It should be notated that the in-wall PM deposition amount is at its upper limit, during the surface PM deposition period. Therefore, during the surface PM deposition period, the saturated adsorption amount of the SCR catalyst 51*a* is constantly at the amount that is achieved when the in-wall PM deposition amount is at its upper limit. From the above, it is considered that the difference between the saturated adsorption amount of the SCR catalyst 51*a* in the state in which PM is deposited in the SCR filter 51 and that in the state in which PM is not deposited in the SCR filter 51 shown in FIG. 4 is attributable to in-wall PM deposition.

The larger the saturated adsorption amount of the SCR catalyst 51*a* is, the less ammonia is apt to be desorbed from the SCR catalyst 51*a*. Therefore, if the values of the other parameters relating to the ammonia desorption quantity are the same, namely if the filter temperature and the ammonia adsorption amount in the SCR catalyst 51*a* are the same, the ammonia desorption quantity is smaller when the in-wall PM deposition amount is large than when the in-wall PM deposition amount is small. Therefore, if the filter temperature and the ammonia adsorption amount in the SCR catalyst 51*a* are the same, the ammonia desorption quantity during the surface PM deposition period is smaller than that during the in-wall PM deposition period. For this reason, it is considered that the ammonia adsorption amount in the SCR catalyst 51*a* is more apt to increase during the surface PM deposition period than during the in-wall PM deposition period. Therefore, the ammonia adsorption amount in the SCR catalyst 51*a* is larger during the surface PM deposition period than during the in-wall PM deposition period, if the values of the other parameters relating to the increase of the ammonia adsorption amount in the SCR catalyst 51*a* are the same.

During the surface PM deposition period, the saturated adsorption amount of the SCR catalyst 51*a* does not increase even if the filter PM deposition amount increases, namely even if the surface PM deposition amount increases. Therefore, during the surface PM deposition period, the ammonia desorption quantity does not change even if the surface PM deposition amount changes, if the filter temperature and the ammonia adsorption amount in the SCR catalyst 51*a* remain the same. For this reason, it is considered that during the surface PM deposition period, increases or decreases in the filter PM deposition amount have little effect on increases or decreases in the ammonia adsorption amount in the SCR catalyst 51*a*.

(Fault Diagnosis)

In this embodiment, in cases where the NOx removal capability of the SCR filter 51 is deteriorated due to deterioration of the SCR catalyst 51*a* or other reasons, the NOx removal rate with the SCR filter 51 decreases. Moreover, the NOx removal rate with the SCR filter 51 decreases also in cases where the quantity of urea solution added decreases due to a trouble of the urea solution addition valve 53, so that the quantity of ammonia supplied to the SCR filter 51 becomes smaller than a required quantity. In this embodiment, both a deterioration of the NOx removal capability of the SCR filter 51 and a trouble of the urea solution addition valve 53 are detected as a fault of the exhaust gas purification system 60 including the SCR filter 51 and the urea solution addition valve 53. In the following, fault diagnosis for detection of a fault of the exhaust gas purification system 60 according to this embodiment will be described.

In this embodiment, a determination as to whether the exhaust gas purification system 60 is faulty or not is made on the basis of the NOx removal rate with the SCR filter 51. More specifically, the NOx removal rate with the SCR filter 51 is calculated from the measurement value of the upstream NOx sensor 57 (i.e. the inflowing NOx concentration) and the measurement value of the downstream NOx sensor 58 (i.e. the outflowing NOx concentration). The inflowing NOx concentration may be estimated on the basis of the operation state of the internal combustion engine 1. If the NOx removal rate with the SCR filter 51 is equal to or lower than a criterion removal rate, it is determined that the exhaust gas purification system 60 is faulty. The criterion removal rate is a value set as a threshold of the NOx removal rate with the SCR filter 51 at or below which it is to be determined that the exhaust gas purification system 60 is faulty.

The value of the NOx removal rate with the SCR filter 51 calculated from the measurement values of the upstream NOx sensor 57 and the downstream NOx sensor 58 varies depending on the ammonia adsorption amount in the SCR catalyst 51*a* at the time of sensor measurement defined as the time at which the measurement values are obtained. As described above, the ammonia adsorption amount in the SCR catalyst 51*a* is larger during the surface PM deposition period than during the in-wall PM deposition period, even if the values of the other parameters relating to the increase of the ammonia adsorption amount in the SCR catalyst 51*a* are the same. Therefore, even if the NOx removal capability of the SCR filter 51 is in the same condition and the quantity of ammonia supplied to the SCR filter 51 is the same, the calculated value of the NOx removal rate with the SCR filter

51 varies depending on whether it is during the surface PM deposition period or the in-wall PM deposition period. Therefore, even if the degree of deterioration of the NOx removal capability of the SCR filter 51 is substantially the same, or even if the decrease in the quantity of ammonia supplied to the SCR filter 51 due to a trouble of the urea solution addition valve 53 is substantially the same, the calculated value of the NOx removal rate with the SCR filter 51 varies. Specifically, the calculated value of the NOx removal rate with the SCR filter 51 is higher in the case where the time of sensor measurement is during the surface PM deposition period than in the case where the time of sensor measurement is during the in-wall PM deposition period.

Figure 6:
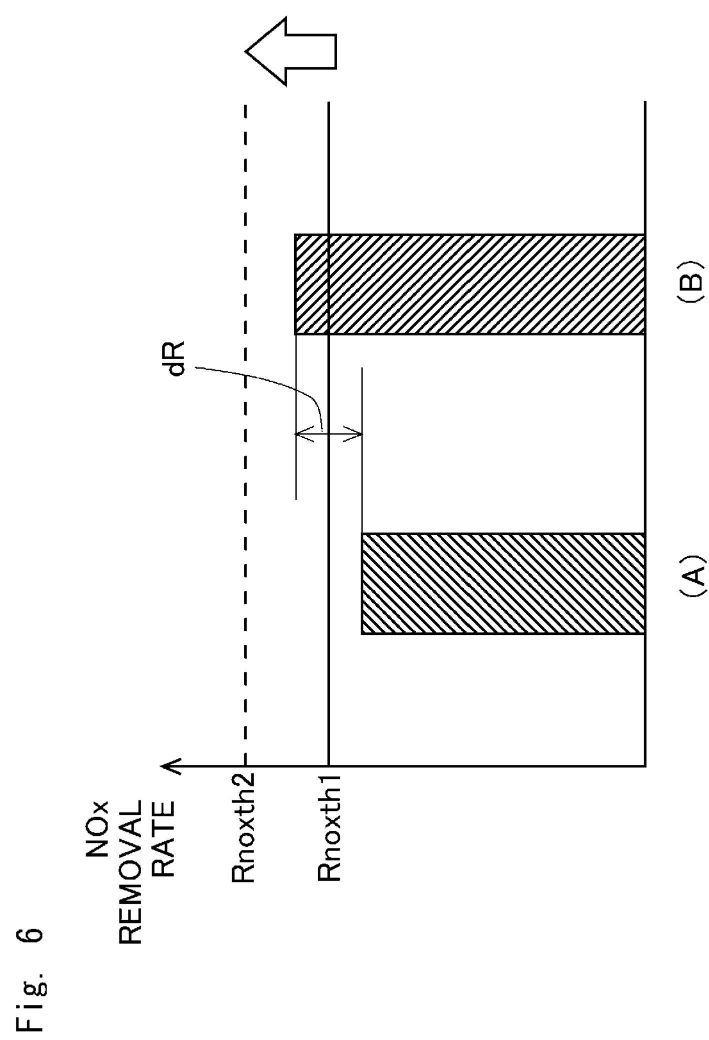
FIG. 6 is a first bar graph showing the NOx removal rate with the SCR filter.

FIG. 6 is a bar graph showing the NOx removal rate with the SCR filter 51. Bars (A) and (B) in FIG. 6 represent values of the NOx removal rate in cases where the exhaust gas purification system 60 is faulty. In both cases represented by bars (A) and (B) in FIG. 6, the NOx removal capability of the SCR filter 51 is in the same condition, and the quantity of ammonia supplied to the SCR filter 51 is the same. Bar (A) in FIG. 6 represents the value of NOx removal rate in a case where the time of sensor measurement is during the in-wall PM deposition period. Bar (B) in FIG. 6 represents the value of the NOx removal rate in a case where the time of sensor measurement is during the surface PM deposition period. The value represented by bar (B) in FIG. 6 is higher than the value represented by bar (A) in FIG. 6 by an NOx removal rate difference dR corresponding to the difference in the ammonia adsorption amount in the SCR catalyst 51*a*. In FIG. 6, Rnoxth1 and Rnoxth2 represent values of the criterion removal rate serving as thresholds for determination of a fault of the exhaust gas purification system.

Let us consider a case where the criterion removal rate is set to Rnoxth1 irrespective of whether the time of sensor measurement is during the surface PM deposition period or the in-wall PM deposition period. In this case, if the time of sensor measurement is during the in-wall PM deposition period as with case (A) in FIG. 6, the NOx removal rate with the SCR filter 51 is lower than or equal to the criterion removal rate Rnoxth1. Then, it is determined that the exhaust gas purification system 60 is faulty. On the other hand, if the time of sensor measurement is during the surface PM deposition period as with case (B) in FIG. 6, there may be cases where the NOx removal rate with the SCR filter 51 is higher than the criterion removal rate Rnoxth1 because the NOx removal rate is higher than that in case (A) in FIG. 6 by the NOx removal rate difference dR. Then, it is mistakenly diagnosed that the exhaust gas purification system 60 is normal, though the exhaust gas purification system 60 is faulty.

In view of the above, in the fault diagnosis according to this embodiment, the criterion removal rate is set to different values depending on whether the time of sensor measurement is during the in-wall PM deposition period or the surface PM deposition period. Specifically, in the case where the time of sensor measurement is during the surface PM deposition period, the value of the criterion removal rate is set to a value higher than that in the case where the time of sensor measurement is during the in-wall PM deposition period. For example, while the value of the criterion removal rate is set to Rnoxth1 in FIG. 6 in the case where the time of sensor measurement is during the in-wall PM deposition period, the value of the criterion removal rate is set to Rnoxth2 (>Rnoxth1) in FIG. 6 in the case where the time of sensor measurement is during the surface PM deposition period. Then, as with case (B) in FIG. 6, even when the NOx removal rate with the SCR filter 51 is higher than that in case (A) in FIG. 6 by the NOx removal rate difference dR, the NOx removal rate is lower than the criterion removal rate Rnoxth2. In consequence, it is determined that the exhaust gas purification system 60 is faulty. Thus, a wrong diagnosis can be prevented from being made in the fault diagnosis of the exhaust gas purification system.

Figure 7:
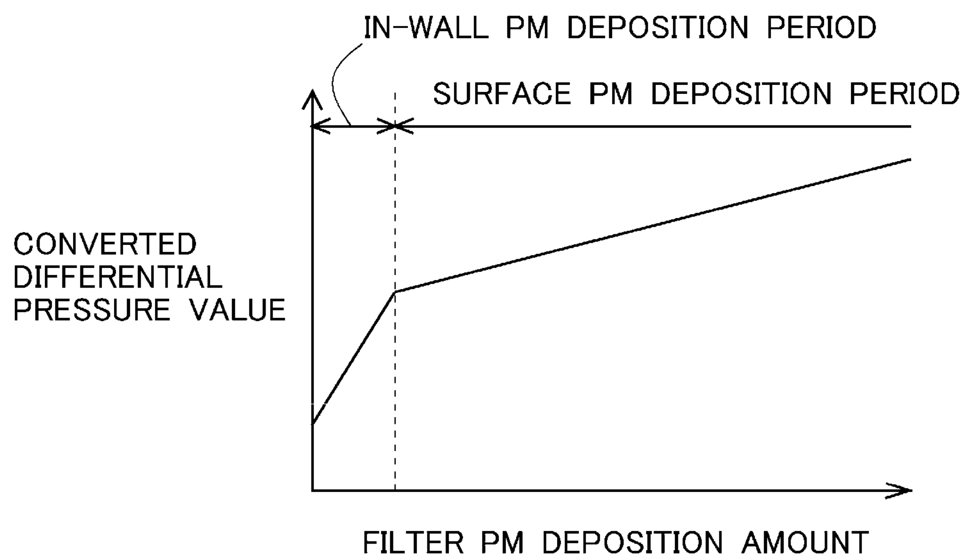
FIG. 7 is a graph showing changes in the converted differential pressure value with increases in the filter PM deposition amount.

Next, a method of making an identification between the in-wall PM deposition period and the surface PM deposition period according to the embodiment will be described with reference to FIG. 7. FIG. 7 is a graph showing changes in the converted differential pressure value with increases in the filter PM deposition amount. In FIG. 7, the horizontal axis represents the filter PM deposition amount and the vertical axis represents the converted differential pressure value.

The converted differential pressure value is a converted value of the filter differential pressure obtained by normalizing the filter differential pressure measured by the differential pressure sensor 59 by the exhaust gas flow rate. More specifically, the converted differential pressure value in this embodiment is expressed by the following equation 1:

$$Ap=dP/Qg \qquad \text{equation 1,}$$

where Ap is the converted differential pressure value, dP is the filter differential pressure (i.e. the measurement value of the differential pressure sensor 59), and Qg is the exhaust gas flow rate.

The differential pressure change rate is defined as the increase in the converted differential pressure value per unit increase in the filter PM deposition amount (i.e. the gradient of the line in FIG. 7). The differential pressure change rate is expressed by the following equation 2:

$$Rp=dAp/dQpm \qquad \text{equation 2,}$$

where Rp is the differential pressure change rate, dAp is the increase in the converted differential pressure value during a third predetermined period, and dQpm is the increase in the filter PM deposition amount during the third predetermined period. The length of the third predetermined period is determined in advance in accordance with the interval of calculation to calculate the differential pressure change rate. The values dAp and dQpm are the increase in the converted differential pressure value and the increase in the filter PM deposition amount respectively during the same third predetermined period.

As shown in FIG. 7, as the filter PM deposition amount increases, the converted differential pressure value increases. With the SCR filter 51, deposition of PM in partition walls affects the filter differential pressure more greatly than deposition of PM on the surface of partition walls. Therefore, for the same amount of increase in the PM deposition amount, the magnitude of increase in the converted differential pressure value is larger with increase in the in-wall PM deposition amount than with increase in the surface PM deposition amount. Therefore, as shown in FIG. 7, the differential pressure change rate is higher during the in-wall PM deposition period than during the surface PM deposition period. In other words, change in the mode of PM deposition in the SCR filter 51 from in-wall PM deposition to surface PM deposition causes a decrease in the differential pressure change rate. Therefore, an identification between the in-wall PM deposition period and the surface PM deposition period can be made on the basis of the differential pressure change rate. Specifically, if the differential pressure change rate is equal to or higher than a specific threshold, it may be concluded that it is during the in-wall PM deposition period. If the differential pressure change rate is lower than the specific threshold, it may be concluded that it is during the surface PM deposition period.

As described above, the mode of PM deposition in the SCR filter 51 shifts in order from in-wall PM deposition to surface PM deposition. It should be noted that oxidation of PM in the SCR filter 51 can occur both inside partition walls and on the surface of partition walls. Therefore, even after the mode of PM deposition has once shifted to surface PM deposition, the in-wall PM deposition amount may decrease due to oxidation in some cases. In such cases, when deposition of PM in the SCR filter 51 restarts, PM deposits firstly in partition walls. Then, there may be cases where the in-wall PM deposition progresses in a state in which PM remains on the surface of partition walls. Therefore, it is difficult to make an identification between the in-wall PM deposition period and the surface PM deposition period with high accuracy only on the basis of the time elapsed since the start of deposition of PM in the SCR filter 51 (e.g. the time elapsed from the end of filter regeneration process) or the filter PM deposition amount (i.e. the overall amount of PM deposited in the SCR filter 51). Using the differential pressure change rate as parameter in making an identification between the in-wall PM deposition period and the surface PM deposition period enables more accurate identification.

(Flow of Fault Diagnosis)

Figure 8:
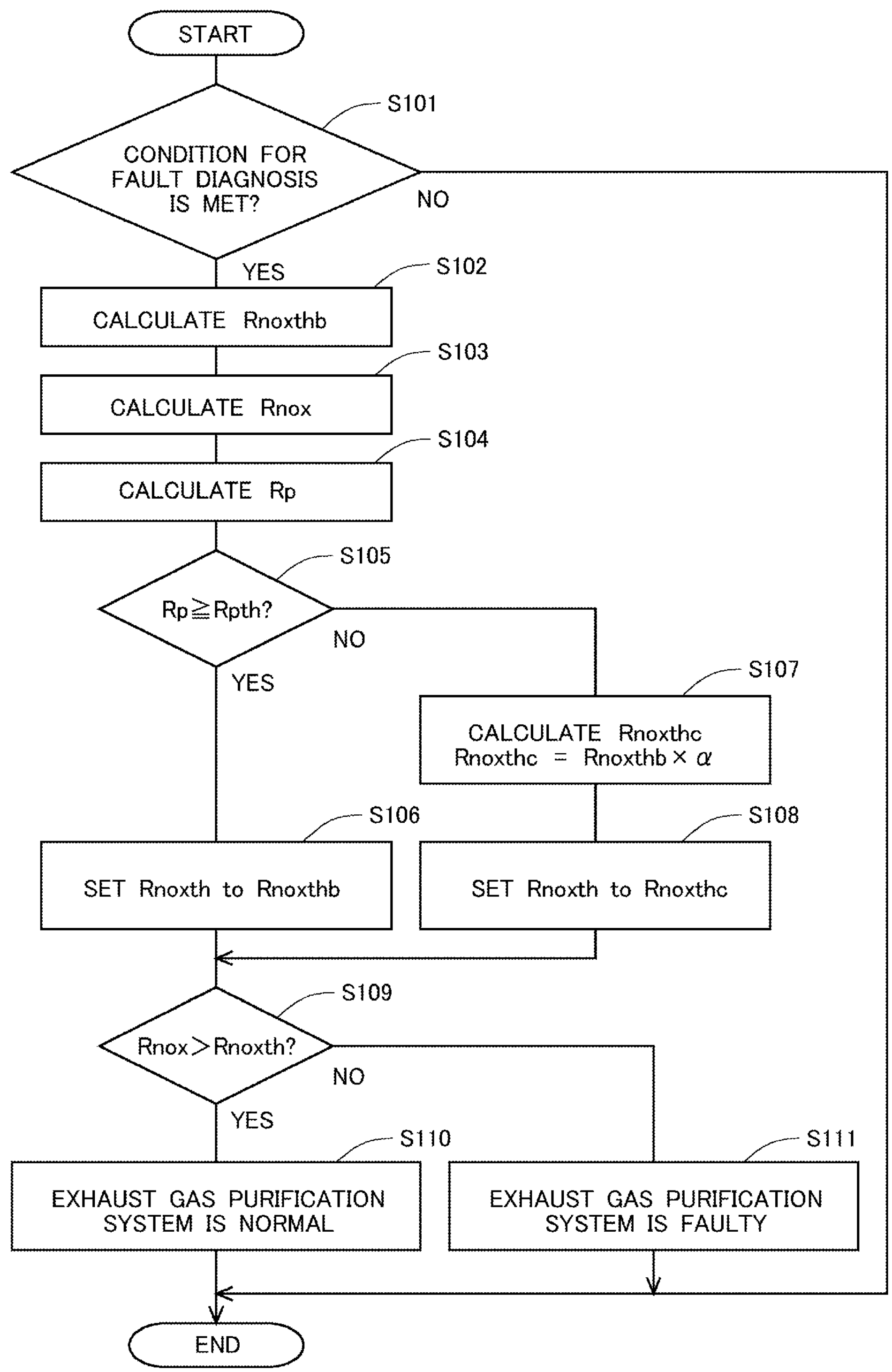
FIG. 8 is a flow chart of fault diagnosis of an exhaust gas purification system according to a first embodiment of the present disclosure.

A flow of fault diagnosis of the exhaust gas purification system according to this embodiment will be described with reference to FIG. 8. FIG. 8 is a flow chart showing the flow of fault diagnosis of the exhaust gas purification system according to the embodiment. Fault diagnosis of the exhaust gas purification system 60 is performed by the ECU 10 according to this flow during operation of the internal combustion engine 1.

In this flow, firstly in step S101, it is determined whether or not conditions for executing the fault diagnosis of the exhaust gas purification system 60 are met. The conditions for executing the fault diagnosis of the exhaust gas purification system 60 are determined in advance. The conditions for executing the fault diagnosis may include, for example, that the internal combustion engine 1 is in a stationary operation state, that the upstream NOx sensor 57 and the downstream NOx sensor 58 are normal, that the exhaust gas flow rate is in a predetermined range, that the inflowing NOx concentration is in a predetermined range, that the filter temperature is in a predetermined range, and that the ammonia adsorption amount in the SCR catalyst 51*a* calculated by the adsorption amount calculation unit 120 is in a predetermined range.

A determination as to whether the upstream NOx sensor 57 and the downstream NOx sensor 58 are normal is made by the ECU 10 in another flow different from this flow, and the result of this determination is memorized in the ECU 10. As described above, in the value of the ammonia adsorption amount in the SCR catalyst 51*a* calculated by the adsorption amount calculation unit 120, the influence of the state of deposition of PM in the SCR filter 51 on the ammonia adsorption amount in the SCR catalyst 51*a* is not taken into account. This value of the ammonia adsorption amount in the SCR catalyst 51*a* calculated by the adsorption amount calculation unit 120 will be sometimes referred to as the "base adsorption amount" hereinafter. The base adsorption amount may be different from the actual ammonia adsorption amount in the SCR catalyst 51*a*, though the base adsorption amount and the actual ammonia adsorption amount correlate with each other to some extent. In making a determination as to whether the conditions for executing the fault diagnosis of the exhaust gas purification system 60 are met, it is sufficient to determine whether or not a quantity of ammonia large enough to perform the fault diagnosis of the exhaust gas purification system 60 is adsorbed in the SCR catalyst 51*a*. Therefore, in making a determination as to whether the conditions for executing the fault diagnosis of the exhaust gas purification system 60 are met, it is not necessarily needed to use the exact value of the ammonia adsorption amount in the SCR catalyst 51*a*. Therefore, the base adsorption amount may be used as a parameter in determining whether or not the fault diagnosis of the exhaust gas purification system 60 may be performed in step S101. As described above, the ammonia adsorption amount in the SCR catalyst 51*a* is affected by the exhaust gas flow rate and the filter temperature. Therefore, when the fault diagnosis of the exhaust gas purification system 60 is performed on the basis of the NOx removal rate in the SCR filter 51, it is desirable that the exhaust gas flow rate and the filter temperature are in respective predetermined ranges.

If the determination made in step S101 is negative, the execution of this process is once terminated. If the determination made in step S101 is affirmative, the processing of step S102 is executed. In step S102, a base criterion removal rate Rnoxthb is calculated using the base adsorption amount calculated by the adsorption amount calculation unit 120. The base criterion removal rate Rnoxthb is calculated as a criterion removal rate that is set in the case where it is assumed that PM is not deposited in the SCR filter 51. In other words, the base criterion removal rate Rnoxthb is a threshold value of the NOx removal rate with the SCR filter 51 in the state in which PM is not deposited therein at or below which a determination that the exhaust gas purification system 60 is faulty is to be made. Relationship between the base adsorption amount and the base criterion removal rate Rnoxthb is determined in advance by, for example, an experiment and stored in the ECU 10 as a map. In step S102, the base criterion removal rate Rnoxthb is calculated using this map.

Then, in step S103, the NOx removal rate Rnox with the SCR filter 51 is calculated. As described above, the NOx removal rate Rnox with the SCR filter 51 is calculated from the measurement value of the upstream NOx sensor 57 as the inflowing NOx concentration and the measurement value of the downstream NOx sensor 58 as the outflowing NOx concentration.

Then, in step S104, the differential pressure change rate Rp at the time of sensor measurement is calculated by equation 2 presented above. The time of sensor measurement mentioned above is the time at which the measurement values of the upstream NOx sensor 57 and the downstream NOx sensor 58 used in the calculation of the NOx removal rate Rnox in step S103 are obtained. Then, in step S105, it is determined whether or not the differential pressure change rate Rp calculated in step S104 is equal to or higher than a predetermined threshold Rpth. The predetermined threshold Rpth is a threshold value with which a distinction between whether the time of sensor measurement is during the in-wall PM deposition period or during the surface PM deposition period is made. This predetermined threshold Rpth is determined in advance by, for example, an experiment and memorized in the ECU 10.

If the determination made in step S105 is affirmative, it may be concluded that the time of sensor measurement is during the in-wall PM deposition period. Then, in step S106, the value of the criterion removal rate Rnoxth is set to the base criterion removal rate Rnoxthb calculated in step S102. If the determination made in step S105 is negative, it may be concluded that the time of sensor measurement is during the surface PM deposition period. Then, in step S107, a corrected criterion removal rate Rnoxthc is calculated by multiplying the base criterion removal rate Rnoxthb calculated in step S102 by a correction coefficient α. The correction coefficient α is a specific value larger than 1. The correction coefficient α is a constant value irrespective of the filter PM deposition amount at the time of sensor measurement. The value of the correction coefficient α is determined in such a way that the corrected criterion removal rate Rnoxthc can serve as a criterion removal rate in the case where the in-wall PM deposition amount in the SCR filter 51 is at its upper limit value. In other words, the corrected criterion removal rate Rnoxthc calculated in step S107 serves as a threshold value of the NOx removal rate with the SCR filter 51 in the state in which the in-wall PM deposition amount is at its upper limit at or below which a determination that the exhaust gas purification system 60 is faulty is to be made. The correction coefficient α as such is determined in advance by, for example, an experiment and memorized in the ECU 10. Then, in step S108, the value of the criterion removal rate Rnoxth is set to the corrected criterion removal rate Rnoxthc calculated in step S107.

The criterion removal rate Rnoxth set in step S108 as above is higher than the criterion removal rate Rnoxth set in step S106. In other words, the criterion removal rate Rnoxth set in the case where the time of sensor measurement is during the surface PM deposition period is higher than the criterion removal rate Rnoxth set in the case where the time of sensor measurement is during the in-wall PM deposition period.

After the processing of step S106 or S108, the processing of step S109 is executed. In step S109, it is determined whether the NOx removal rate Rnox with the SCR filter 51 calculated in step S103 is higher than the criterion removal rate Rnoxth set in step S106 or S108. If the determination made in step S109 is affirmative, it is determined that the exhaust gas purification system 60 is normal in the next step S110. On the other hand, if the determination made in step S109 is negative, namely if the NOx removal rate Rnox with the SCR filter 51 is equal to or lower than the criterion removal rate Rnoxth, it is determined that the exhaust gas purification system 60 is faulty in the next step S111. After it is determined that the exhaust gas purification system 60 is normal in step S110, or after it is determined that the exhaust gas purification system 60 is faulty in step S111, the execution of this flow is terminated.

According to the above-described flow of fault diagnosis, even when the calculated value of the NOx removal rate Rnox with the SCR catalyst 51*a* is a value affected by the state of deposition of PM in the SCR filter 51, the criterion removal rate Rnoxth to be compared with the NOx removal rate in fault diagnosis of the exhaust gas purification system is set to a more appropriate value. Therefore, the accuracy of fault diagnosis of the exhaust gas purification system can be improved.

On the basis of the conventional theory that increases in the PM deposition amount in an SCR filter make the ammonia adsorption amount in the SCR catalyst supported on that SCR filter more apt to increase, the fault diagnosis process may be designed in such a way that the value of the criterion removal rate Rnoxth is varied depending on the filter PM deposition amount in the case where the time of sensor measurement is during the surface PM deposition period. Specifically, the fault diagnosis process may be designed in such a way that the larger the filter PM deposition amount at the time of sensor measurement is (namely, the larger the surface PM deposition amount is), the larger the correction coefficient α used in calculation of the corrected criterion removal rate Rnoxthc in the processing of step S107 in the above-described flow of fault diagnosis is made so that the larger the filter PM deposition amount at the time of sensor measurement is, the higher the value of the criterion removal rate Rnoxth is made. However, according to the findings made by the inventors of the present disclosure, increases or decreases in the surface PM deposition amount have little effect on the ammonia adsorption amount in the SCR catalyst, as described above. Therefore, increases or decreases in the PM deposition amount during the surface PM deposition period have little effect on the NOx removal rate with the SCR filter. Therefore, in the case where the time of sensor measurement is during the surface PM deposition period, if the criterion removal rate Rnoxth is varied depending on the filter PM deposition amount, there is a possibility that the accuracy of fault diagnosis of the exhaust gas purification system may be deteriorated. In the case of the above-described flow of fault diagnosis, the correction coefficient α is set as a constant value irrespective of the filter PM deposition amount at the time of sensor measurement. Thus, in the case where the differential pressure change rate Rp at the time of sensor measurement is lower than the predetermined threshold Rpth, the change of the value of the criterion removal rate Rnoxth with a change in the Filter PM deposition amount at the time of sensor measurement is zero. Therefore, according to the above-described flow of fault diagnosis, in the case where the time of sensor measurement is during the surface PM deposition period, the filter PM deposition amount at the time of sensor measurement does not affect the set value of the criterion removal rate Rnoxth. Thus, the criterion removal rate Rnoxth in the case where the time of sensor measurement is during the surface PM deposition period is set to a more appropriate value. Therefore, the accuracy of fault diagnosis of the exhaust gas purification system in the case where the time of sensor measurement is during the surface PM deposition period can be improved.

As shown in FIG. 4, at the same filter temperature, the saturated adsorption amount of the SCR catalyst 51*a* is larger in the state in which PM is deposited in the SCR filter 51 than in the state in which PM is not deposited in the SCR filter 51. As described above, this change in the saturated adsorption amount of the SCR catalyst 51*a* is attributable not to surface PM deposition but to in-wall PM deposition. Moreover, as will be seen from FIG. 4, the lower the filter temperature is, the larger the magnitude of increase of the saturated adsorption amount of the SCR catalyst 51*a* attributable to in-wall PM deposition is. Therefore, even during the surface PM deposition period, in which the in-wall PM deposition amount remains constant at its upper limit, the lower the filter temperature is, the larger the magnitude of decrease of the ammonia desorption quantity attributable to in-wall PM deposition is, when the ammonia adsorption amount in the SCR catalyst 51*a* is the same. Accordingly, the lower the temperature of the SCR filter 51 is, the larger the magnitude of increase in the ammonia adsorption amount in the SCR catalyst 51*a* attributable to deposition of PM in partition walls of the SCR filter 51 is. Therefore, the lower the temperature of the SCR filter 51 is, the larger the difference between the NOx removal rate in the state in which the in-wall PM deposition amount is at its upper limit and the NOx removal rate in the state in which PM is not deposited in the SCR filter 51 is. In other words, during the surface PM deposition period, the lower the temperature of the SCR filter 51 is, the higher the NOx removal rate is, if the values of the parameters relating to the NOx removal rate other than the temperature of the SCR filter 51 are the same.

Figure 9:
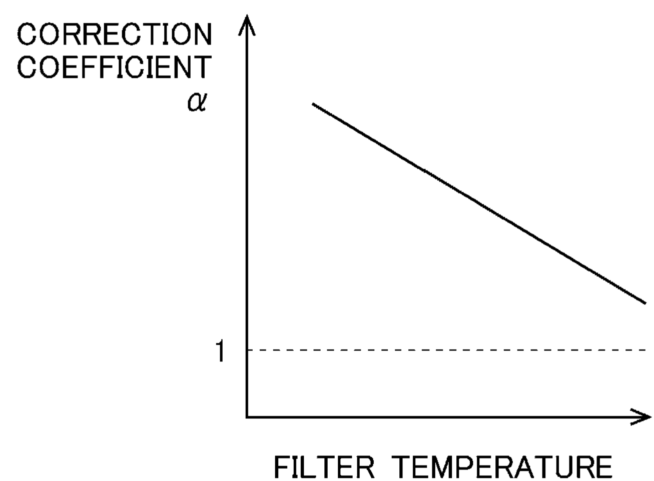
FIG. 9 is a graph showing relationship between the filter temperature and the correction coefficient α according to the first embodiment of the present disclosure.

In view of the above, in this embodiment, the value of the correction coefficient α used in the calculation of the corrected criterion removal rate Rnoxthc in step S107 of the above-described flow of fault diagnosis may be varied depending on the filter temperature at the time of sensor measurement. FIG. 9 is a graph showing relationship between the filter temperature and the correction coefficient α. As shown in FIG. 9, the correction coefficient α may be made larger when filter temperature at the time of sensor measurement is low than when the filter temperature is high. Thus, in the case where the differential pressure change rate Rp at the time of sensor measurement is lower than the predetermined threshold Rpth, namely in the case where the time of sensor measurement is during the surface PM deposition period, the value of the criterion removal rate Rnoxth is set higher when the filter temperature at the time of sensor measurement is low than when the filter temperature at the time of sensor measurement is high. Thus, the criterion removal rate Rnoxth in the case where the time of sensor measurement is during the surface PM deposition period can be set to a more appropriate value. Therefore, the accuracy of fault diagnosis of the exhaust gas purification system in the case where the time of sensor measurement is during the surface PM deposition period can be further improved.

In the above-described flow of fault diagnosis, in the case where the differential pressure change rate Rp at the time of sensor measurement is equal to or higher than the predetermined threshold Rpth, namely in the case where the time of sensor measurement is during the in-wall PM deposition period, the value of the criterion removal rate Rnoxth is set equal to the base criterion removal rate Rnoxthb irrespective of the in-wall PM deposition amount at the time of sensor measurement. The value of the base criterion removal rate Rnoxthb is calculated as the criterion removal rate that is set in the case where it is assumed that PM is not deposited in the SCR filter 51, as described above.

In the case where the time of sensor measurement is during the in-wall PM deposition period, the value of the NOx removal rate varies depending on the in-wall PM deposition amount at the time of sensor measurement, if the values of the other parameters relating to the NOx removal rate with the SCR filter 51 are the same. Therefore, in the case where the time of sensor measurement is during the in-wall PM deposition period, it is theoretically preferred that the criterion removal rate Rnoxth be set to a value adapted to the in-wall PM deposition amount at the time of sensor measurement. However, as described above, even if the filter PM deposition amount is the same, the in-wall PM deposition amount is not necessarily the same, because oxidation of PM can occur both in the partition walls of the SCR filter 51 and on the surface of the partition walls. Moreover, even if the in-wall PM deposition amount is the same, the converted differential pressure value varies if the surface PM deposition amount varies. For this reason, it is difficult to determine the in-wall PM deposition amount during the in-wall PM deposition period accurately from the filter PM deposition amount and the converted differential pressure value. Therefore, in this embodiment, in the case where the time of sensor measurement is during the in-wall PM deposition period, the base criterion removal rate Rnoxthb is used as the criterion removal rate Rnoxth. Nonetheless, it is not essential that the criterion removal rate Rnoxth in the case where the time of sensor measurement is in the in-wall PM deposition period be set to the base criterion removal rate Rnoxthb. For example, an assumption that the in-wall PM deposition amount changes to some extent during the in-wall PM deposition period may be made in advance, and the criterion removal rate Rnoxth may be set on the basis of that assumption. In this case, it is preferred that the value of the criterion removal rate Rnoxth be made higher when the assumed in-wall PM deposition amount at the time of sensor measurement is large than when the assumed in-wall PM deposition amount is small. Even in the case where the value of the criterion removal rate Rnoxth in the case where the time of sensor measurement is during the in-wall PM deposition period is set in this way, the value of the criterion removal rate thus set is lower than the value of the criterion removal rate Rnoxth in the case where the time of sensor measurement is during the surface PM deposition period.

In the above-described embodiment, the SCR filter 51 corresponds to the SCR filter according to the first aspect of the present disclosure, and the urea solution addition valve 53 corresponds to the ammonia supply device according to the first aspect of the present disclosure. Moreover, in the above-described embodiment, the downstream NOx sensor 58 corresponds to the NOx sensor according to the first aspect of the present disclosure. Furthermore, in the above-described embodiment, the execution of the processing of steps S109 to S111 in the flow of fault diagnosis shown in FIG. 8 by the ECU 10 embodies the determination unit according to the first aspect of the present disclosure. Still further, in the above-described embodiment, the execution of the processing of steps S105, S106, S107, and S108 in the flow of fault diagnosis shown in FIG. 8 by the ECU 10 embodies the setting unit according to the first aspect of the present disclosure.

(Modification)

In the above-described embodiment, the base criterion removal rate is calculated on the basis of the base adsorption amount, which is the ammonia adsorption amount calculated by the adsorption amount calculation unit 120. In other words, the base criterion removal rate Rnoxthb is set as a criterion removal rate in the case where it is assumed that PM is not deposited in the SCR filter 51. Alternatively, the base criterion removal rate Rnoxthb may be set as a criterion removal rate in the case where it is assumed that the in-wall PM deposition amount in the SCR filter is at its upper limit value. In this case, in the case where the differential pressure change rate Rp at the time of sensor measurement is lower than the predetermined threshold Rpth, namely in the case where the time of sensor measurement is during the surface PM deposition period, the criterion removal rate Rnoxth used as the threshold for determination of a fault of the exhaust gas purification system is set to the base criterion removal rate Rnoxthb. In the case where the differential pressure change rate Rp at the time of sensor measurement is equal to or higher than the predetermined threshold Rpth, namely in the case where the time of sensor measurement is during the in-wall PM deposition period, the corrected criterion removal rate Rnoxthc is calculated by multiplying the base criterion removal rate Rnoxthb by a correction coefficient α'. The value of the correction coefficient α' is larger than 0 and smaller than 1. Therefore, the value of the corrected criterion removal rate Rnoxthc is lower than the base criterion removal rate Rnoxthb. Then, the criterion removal rate Rnoxth serving as the threshold for determination of a fault of the exhaust gas purification system is set to the corrected criterion removal rate Rnoxthc. In the case where the criterion removal rate Rnoxth is set in this way also, the value of the criterion removal rate in the case where the time of sensor measurement is during the surface PM deposition period is higher than the value of the criterion removal rate in the case where the time of sensor measurement is during the in-wall PM deposition period. Therefore, the criterion removal rate to be compared with the NOx removal rate with the SCR filter 51 in determining a fault of the exhaust gas purification system is set to more appropriate value.

Embodiment 2

The general configuration of an internal combustion engine and its air-intake and exhaust systems according to a second embodiment is the same as that according to the first embodiment. In the following, features of fault diagnosis of an exhaust gas purification system according to the second embodiment that are different from those according to the first embodiment will be described.

In the fault diagnosis of the exhaust gas purification system according to the first embodiment, the value of the criterion removal rate serving as a threshold to be compared with the NOX removal rate with the SCR filter 51 is set to different values depending on whether the time of sensor measurement is during the in-wall PM deposition period or the surface PM deposition period. In the fault diagnosis of the exhaust gas purification system according to the second embodiment, a corrected NOx removal rate is calculated by correcting the NOx removal rate with the SCR filter 51 calculated from the measurement values of the upstream NOx sensor 57 and the downstream NOx sensor 58 into different values depending on whether the time of sensor measurement is during the in-wall PM deposition period or the surface PM deposition period. Then, the corrected removal rate is compared with the base criterion removal rate to determine whether the exhaust gas purification system 60 is faulty or not.

Figure 10:
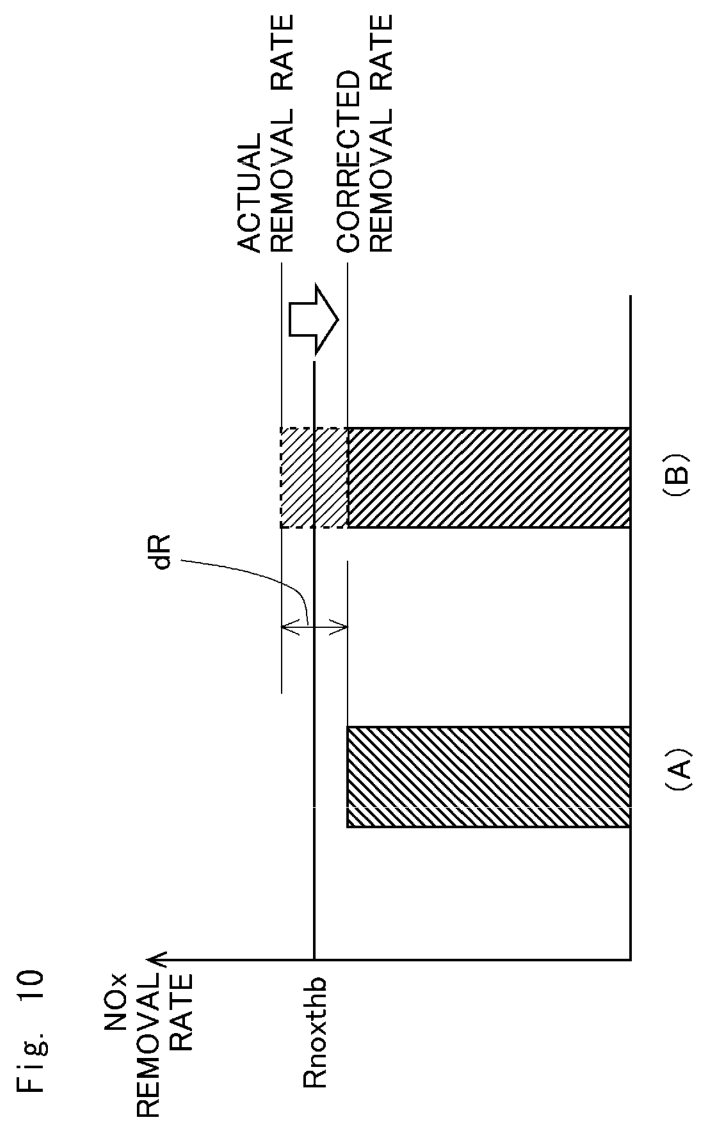
FIG. 10 a second bar graph showing the NOx removal rate with the SCR filter.

FIG. 10 is a bar graph similar to FIG. 6 showing the NOx removal rate with the SCR filter 51. Bars (A) and (B) in FIG. 10 represent values of the NOx removal rate in cases where the exhaust gas purification system 60 is faulty. In both cases represented by bars (A) and (B) in FIG. 10, the NOx removal capability of the SCR filter 51 is in the same condition, and the quantity of ammonia supplied to the SCR filter 51 is the same. Bar (A) in FIG. 10 represents the value of NOx removal rate in a case where the time of sensor measurement is during the in-wall PM deposition period. Bar (B) in FIG. 10 represents the value of the NOx removal rate in a case where the time of sensor measurement is during the surface PM deposition period. The value represented by bar (B) in FIG. 10 is higher than the value represented by bar (A) in FIG. 10 by an NOx removal rate difference dR corresponding to the difference in the ammonia adsorption amount in the SCR catalyst 51*a*. In FIG. 10, Rnoxthb is the base criterion removal rate.

In case (A) in FIG. 10, the NOx removal rate with the SCR filter 51 is lower than the base criterion removal rate Rnoxthb. Thus, in the case where the time of sensor measurement is during the in-wall PM deposition period, if a determination as to whether or not the exhaust gas purification system 60 is faulty is made by comparing the NOx removal rate with the SCR filter 51 calculated from the measurement values of the upstream NOx sensor 57 and the downstream NOx sensor 58 (which will be sometimes referred to as the "actual removal rate" hereinafter) with the base criterion removal rate, it is determined that the exhaust gas purification system 60 is faulty. On the other hand, in case (b) in FIG. 10, the NOx removal rate with the SCR catalyst 51 is higher than that in case (A) in FIG. 10 by the NOx removal rate difference dR, and hence the actual removal rate is higher than the base criterion removal rate Rnoxthb. Therefore, in the case where the time of sensor measurement is during the surface PM deposition period, if a determination as to whether or not the exhaust gas purification system 60 is faulty is made by comparing the actual removal rate with the base criterion removal rate, it is mistakenly determined that the exhaust gas purification system 60 is normal, though the exhaust gas purification system 60 is faulty.

In this embodiment, a corrected removal rate is calculated by correcting the actual removal rate calculated from the measurement value of the upstream NOx sensor 57 and the downstream NOx sensor 58 by using a correction coefficient having different values depending on whether the time of sensor measurement is during the in-wall PM deposition period or the surface PM deposition period. Then, the corrected removal rate thus calculated and the base criterion removal rate are compared to determine whether the exhaust gas purification system 60 is faulty. Specifically, in the case where the time of sensor measurement is during the surface PM deposition period, the actual removal rate is converted into a lower corrected removal rate by correction. In other words, the corrected removal rate is calculated as a value equal to the actual removal rate minus the increase in the NOX removal rate resulting from in-wall PM deposition. Therefore, even in the case where the actual removal rate becomes higher like in case (B) in FIG. 10 as compared to case (A) in FIG. 10, it is determined that the exhaust gas purification system 60 is faulty, if the corrected removal rate is equal to or lower than the base criterion removal rate Rnoxthb. Therefore, a wrong determination can be prevented from being made in fault diagnosis of the exhaust gas purification system.

In this embodiment also, the method of determining whether the time of sensor measurement is during the in-wall PM deposition period or the surface PM deposition period is the same as that in the first embodiment. Specifically, a determination as to whether the time of sensor measurement is during the in-wall PM deposition period or the surface PM deposition period is made on the basis of whether or not the differential pressure change rate at the time of sensor measurement is lower than the predetermined threshold.

(Flow of Fault Diagnosis)

Figure 11:
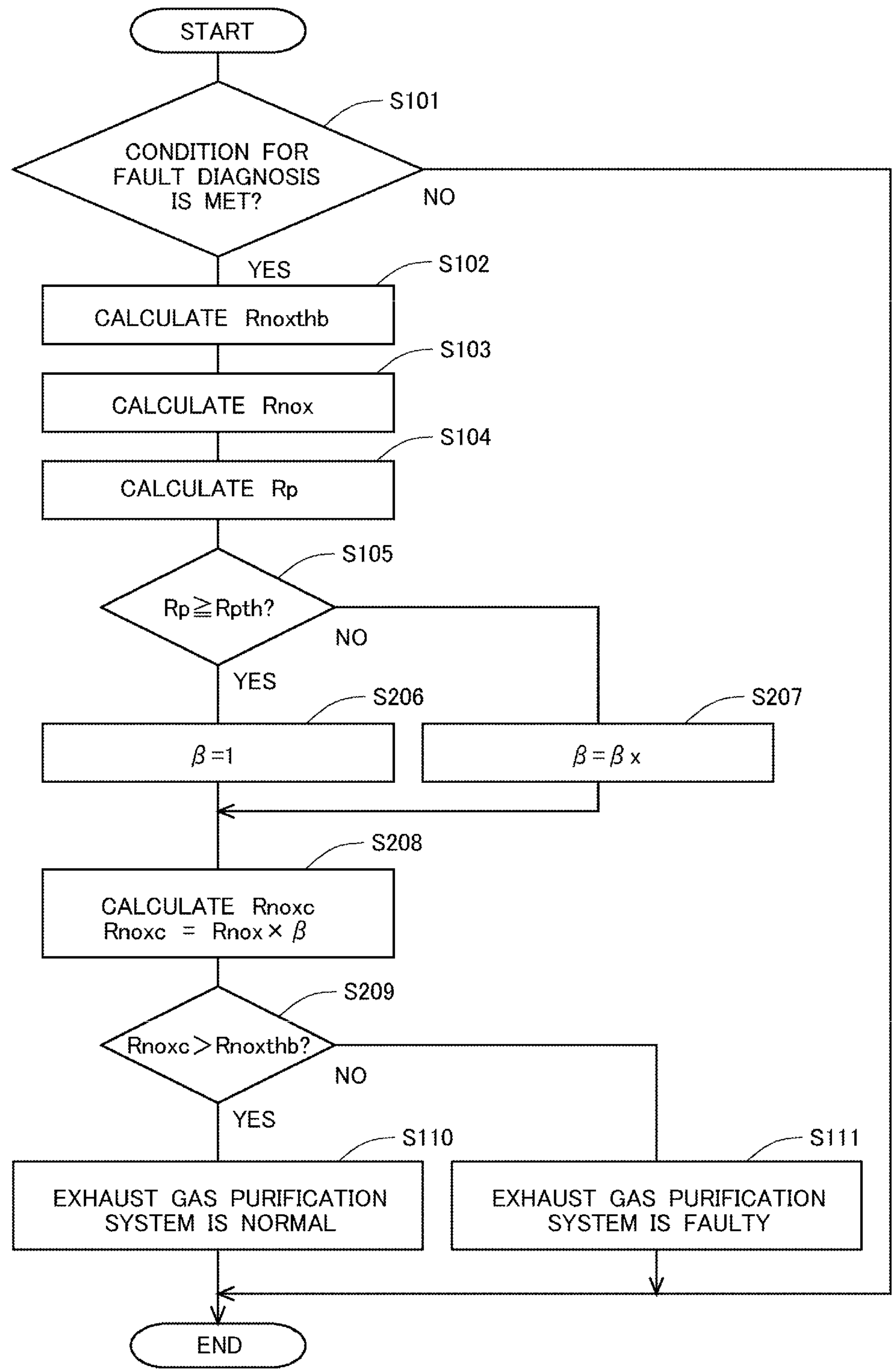
FIG. 11 is a flow chart of fault diagnosis of an exhaust gas purification system according to a second embodiment of the present disclosure.

FIG. 11 is a flow chart showing the flow of fault diagnosis of the exhaust gas purification system according to the second embodiment. Fault diagnosis of the exhaust gas purification system 60 is performed by the ECU 10 according to this flow during operation of the internal combustion engine 1. In this flow of processing, the steps in which the processing same as that in the flow of processing shown in FIG. 8 is executed are denoted by the same reference signs and will not be described further.

In this flow, if the determination made in step S105 is affirmative, namely if the time of sensor measurement is during the in-wall PM deposition period, the processing of step S206 is executed next. In step S206, a correction coefficient β to be used in calculation of corrected removal rate Rnoxc in step S208, which will be described later, is set to 1. If the determination made in step S105 is negative, namely if the time of sensor measurement is during the surface PM deposition period, the processing of step S207 is executed next. In step S207, the correction coefficient β to be used in calculation of corrected removal rate Rnoxc in step S208, which will be described later, is set to a predetermined value βx. This predetermined value βx is larger than 0 and smaller than 1. This predetermined value βx is a fixed value irrespective of the filter PM deposition amount at the time of sensor measurement. The predetermined value βx is determined as such a value that makes the corrected removal rate Rnoxc equal to the NOx removal rate with the SCR filter 51 in which PM is not deposited. In other words, the corrected removal rate Rnoxc calculated using the predetermined value βx as the correction coefficient β is equal to the NOx removal rate Rnox with the SCR filter 51 (or the actual NOx removal rate) calculated in step S103 minus the increase in the NOx removal rate resulting from in-wall PM deposition. The predetermined value βx as such is determined in advance by, for example, an experiment and memorized in the ECU 10.

After the processing of step S206 or S207, the processing of step S208 is executed. In step S208, the corrected removal rate Rnoxc is calculated by multiplying the actual removal rate Rnox calculated in step S103 by the correction coefficient β determined in step S206 or S207. With the corrected removal rate Rnoxc determined in the above-described manner, in the case where the determination made in step S105 is affirmative, namely in the case where the time of sensor measurement is during the in-wall PM deposition period, the actual removal rate Rnox calculated in step S103 serves as the corrected removal rate Rnoxc without change in its value (namely, Rnoxc=Rnox). On the other hand, in the case where the determination made in step S105 is negative, namely in the case where the time of sensor measurement is during the surface PM deposition period, the corrected removal rate Rnoxc has a value lower than the actual removal rate Rnox calculated in step S103 by decreasing correction (namely, Rnoxc<Rnox). Therefore, the decrease in the value from the actual removal rate Rnox to the corrected removal rate Rnoxc in the case where the time of sensor measurement is during the surface PM deposition period is larger than the decrease in the value from the actual removal rate Rnox to the corrected removal rate Rnoxc in the case where the time of sensor measurement is during the in-wall PM deposition period (the decrease=0, in the latter case).

After the processing of step S208, the processing of step S209 is executed. In step S209, it is determined whether or not the corrected removal rate Rnoxc is higher than the base criterion removal rate Rnoxthb calculated in step S102. If the determination made in step S209 is affirmative, it is determined that the exhaust gas purification system 60 is normal, in the next step S110. On the other hand, if the determination made in step S209 is negative, namely if the corrected removal rate Rnoxc is equal to or lower than the base criterion removal rate Rnoxthb, it is determined that the exhaust gas purification system 60 is faulty, in the next step S111.

In the above-described flow of fault diagnosis, even if the calculated value of the NOx removal rate Rnox (actual removal rate) with the SCR catalyst 51*a* is affected by the state of deposition of PM in the SCR filter 51, the corrected removal rate Rnoxc to be compared with the base criterion removal rate Rnoxthb in determining a fault of the exhaust gas purification system is set to a more appropriate value. Therefore, the accuracy of fault diagnosis of the exhaust gas purification system can be improved.

On the basis of the conventional theory that increases in the PM deposition amount in an SCR filter make the ammonia adsorption amount in the SCR catalyst supported on that SCR filter more apt to increase, the decrease from the actual removal rate Rnox to the corrected removal rate Rnoxc (or the difference between the actual removal rate Rnox to the corrected removal rate Rnoxc) may be varied depending on the filter PM deposition amount, in the case where the time of sensor measurement is during the surface PM deposition period. Specifically, the larger the filter PM deposition amount at the time of sensor measurement is (namely, the larger the surface PM deposition amount is), the smaller the value βx set as the correction coefficient β in the processing of step S207 in the above-described flow of fault diagnosis may be made, so that the larger the filter PM deposition amount at the time of sensor measurement is, the larger the decrease from the actual removal rate Rnox to the corrected removal rate Rnoxc is. However, according to the findings made by the inventors of the present disclosure, varying the decrease from the actual removal rate Rnox to the corrected removal rate Rnoxc depending on the filter PM deposition amount can lead to deterioration in the accuracy of fault diagnosis of the exhaust gas purification system. In the above-described fault diagnosis process, the value of βx is fixed irrespective of the filter PM deposition amount at the time of sensor measurement. Therefore, in the case where the differential pressure change rate Rp at the time of sensor measurement is lower than the predetermined threshold Rpth, the change in the decrease from the actual removal rate Rnox to the corrected removal rate Rnoxc with a change in the filter PM deposition amount at the time of sensor measurement is zero. In other words, in the above-described fault diagnosis process, in the case where the time of sensor measurement is during the surface PM deposition period, the calculation of the corrected removal rate Rnox is not affected by the filter PM deposition amount at the time of sensor measurement. Therefore, the corrected removal rate Rnoxc in the case where the time of sensor measurement is during the surface PM deposition period is set to a more appropriate value. Therefore, the accuracy of fault diagnosis of the exhaust gas purification system in the case where the time of sensor measurement is during the surface PM deposition period can be improved.

Figure 12:
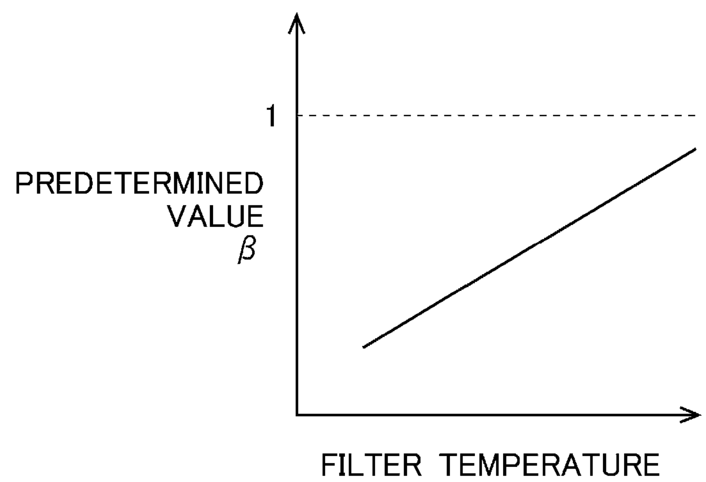
FIG. 12 is a graph showing relationship between the filter temperature and the predetermined value βx according to the second embodiment of the present disclosure.

As described above, during the surface PM deposition period, the lower the temperature of the SCR filter 51 is, the higher the actual removal rate is, if the values of the parameters relating to the NOx removal rate other than the temperature of the filter 51 remain the same. In this embodiment, the predetermined value βx set as the correction coefficient β in step S207 in the above-described flow of fault diagnosis may be varied depending on the filter temperature at the time of sensor measurement. FIG. 12 is a graph showing relationship between the filter temperature and the predetermined value βx. As shown in FIG. 12, the predetermined value βx may be made smaller when the filter temperature at the time of sensor measurement is low than when the filter temperature is high. In this case, in the case where the differential pressure change rate Rp at the time of sensor measurement is lower than the predetermined threshold Rpth, namely in the case where the time of sensor measurement is during the surface PM deposition period, the calculated value of the corrected removal rate Rnoxc is lower when the filter temperature at the time of sensor measurement is low than when the filter temperature is high. In other words, in the case where the time of sensor measurement is during the surface PM deposition period, the decrease from the actual removal rate Rnox to the corrected removal rate Rnoxc is larger when the filter temperature at the time of sensor measurement is low than when the filter temperature is high. Therefore, the corrected removal rate Rnoxc in the case where the time of sensor measurement is during the surface PM deposition period is set to a more appropriate value. Therefore, the accuracy of fault diagnosis of the exhaust gas purification system in the case where the time of sensor measurement is during the surface PM deposition period can further be improved.

In the above-described flow of fault diagnosis, in the case where the differential pressure change rate Rp at the time of sensor measurement is equal to or higher than the predetermined threshold Rpth, namely in the case where the time of sensor measurement is during the in-wall PM deposition period, the intact value of the actual removal rate Rnox serves as the value of the corrected removal rate Rnoxc irrespective of the in-wall PM deposition amount at the time of sensor measurement. In the case where the time of sensor measurement is during the in-wall PM deposition period also, the value of the actual removal rate Rnox contains an increase in the NOx removal rate attributable to deposition of PM in partition walls of the SCR filter 51.

Therefore, in the case where the time of sensor measurement is during the in-wall PM deposition period, the actual removal rate Rnox varies depending on the in-wall PM deposition amount at the time of sensor measurement even if the values of the other parameters relating to the NOx removal rate with the SCR filter 51 are the same. Therefore, in the case where the time of sensor measurement is during the in-wall PM deposition period also, it is theoretically preferred in calculating the corrected removal rate Rnoxc that the actual removal rate Rnox be converted into a lower corrected removal rate Rnoxc by correction taking account of the in-wall PM deposition amount at the time of sensor measurement. However, as described above, it is difficult to determine the in-wall PM deposition amount during the in-wall PM deposition period correctly. Therefore, in this embodiment, in the case where the time of sensor measurement is during the in-wall PM deposition period, the intact value of the actual removal rate Rnox is used as the corrected removal rate Rnox. Nevertheless, the value of the corrected removal rate Rnoxc in the case where the time of sensor measurement is during the in-wall PM deposition period is not necessarily required to be set to the intact value of the actual removal rate Rnox. For example, an assumption that the in-wall PM deposition amount changes to some extent during the in-wall PM deposition period may be made in advance, and the actual removal rate Rnox may be converted into a lower corrected removal rate Rnoxc by correction on the basis of this assumption. In this case, it is preferred that the calculated value of the corrected removal rate Rnoxc be made lower when the assumed in-wall PM deposition amount at the time of sensor measurement is large than when the assumed in-wall PM deposition amount is small. In other words, it is preferred that the decrease from the actual removal rate Rnox to the corrected removal rate Rnoxc be made larger when the assumed in-wall PM deposition amount at the time of sensor measurement is large than when the assumed in-wall PM deposition amount is small. Even in the case where the corrected removal rate Rnoxc in the case where the time of sensor measurement is during the in-wall PM deposition period is calculated in the above-described manner, the decrease from the actual removal rate Rnox to the corrected removal rate Rnoxc is smaller than the decrease from the actual removal rate Rnox to the corrected removal rate Rnoxc in the case where the time of sensor measurement is during the surface PM deposition period.

In the above-described embodiment, the SCR filter 51 corresponds to the SCR filter according to the second aspect of the present disclosure, and the urea solution addition valve 53 corresponds to the ammonia supply device according to the second aspect of the present disclosure. Moreover, in the above-described embodiment, the downstream NOx sensor 58 corresponds to the NOx sensor according to the second aspect of the present disclosure. Furthermore, in the above-described embodiment, the execution of the processing of steps S209, S110, and S111 in the flow of fault diagnosis shown in FIG. 11 by the ECU 10 embodies the determination unit according to the second aspect of the present disclosure. Still further, in the above-described embodiment, the execution of the processing of steps S105, S206, S207, and S208 in the flow of fault diagnosis shown in FIG. 11 by the ECU 10 embodies the corrected removal rate calculation unit according to the second aspect of the present disclosure.

This application claims the benefit of Japanese Patent Application No. 2015-232467, filed on Nov. 27, 2015, which is hereby incorporated by reference herein in its entirety.

What is claimed is:

1. A fault diagnosis apparatus for an exhaust gas purification system for diagnosing whether or not the exhaust gas purification system is faulty, the exhaust gas purification system including an SCR filter provided in an exhaust passage of an internal combustion engine and an ammonia supply device that supplies ammonia to said SCR filter, said SCR filter including a filter and an SCR catalyst supported on said filter, said SCR catalyst having a capability of reducing NOx in exhaust gas by using ammonia as reducing agent, and said filter having a function of trapping particulate matter in exhaust gas, comprising:

an NOx sensor provided in the exhaust passage downstream of said SCR filter;

an NOx removal rate calculation unit configured to calculate the NOx removal rate with said SCR filter by using a measurement value of said NOx sensor;

a determination unit configured to determine that said exhaust gas purification system is faulty, if the NOx removal rate with said SCR filter calculated by said NOx removal rate calculation unit is equal to or lower than a predetermined criterion removal rate; and a setting unit configured to set said criterion removal rate, wherein said setting unit sets the value of said criterion removal rate higher when a differential pressure change rate at a time of sensor measurement is lower than a predetermined threshold than when said differential pressure change rate is equal to or higher than said predetermined threshold, said differential pressure change rate being defined as the amount of increase in a converted differential pressure value obtained by normalizing the differential pressure of the exhaust gas across said SCR filter by the exhaust gas rate per unit increase in a filter PM deposition amount defined as the amount of particulate matter deposited in said SCR filter that is estimated on the basis of a parameter other than said converted differential pressure value, and said time of sensor measurement being defined as the time at which the measurement value of said NOx sensor used in calculation of the NOx removal rate by said NOx removal rate calculation unit is obtained.

2. A fault diagnosis apparatus for an exhaust gas purification system according to claim 1, wherein in the case where said differential pressure change rate at said time of sensor measurement is lower than said predetermined threshold, a change in said criterion removal rate set by said setting unit relative to a change in said filter PM deposition amount at said time of sensor measurement is zero.

3. A fault diagnosis apparatus for an exhaust gas purification system according to claim 1, wherein in the case where said differential pressure change rate at said time of sensor measurement is lower than said predetermined threshold, said setting unit sets the value of said criterion removal rate higher when the temperature of said SCR filter at said time of sensor measurement is low than when said temperature of said SCR filter at said time of sensor measurement is high.

4. A fault diagnosis apparatus for an exhaust gas purification system for diagnosing whether or not the exhaust gas purification system is faulty, the exhaust gas purification system including an SCR filter provided in an exhaust passage of an internal combustion engine and an ammonia supply device that supplies ammonia to said SCR filter, said SCR filter including a filter and an SCR catalyst supported on said filter, said SCR catalyst having a capability of reducing NOx in exhaust gas by using ammonia as reducing agent, and said filter having a function of trapping particulate matter in exhaust gas, comprising:

an NOx sensor provided in the exhaust passage downstream of said SCR filter;

an NOx removal rate calculation unit configured to calculate the NOx removal rate with said SCR filter by using a measurement value of said NOx sensor;

a corrected removal rate calculation unit configured to calculate a corrected removal rate by subtracting a decrease that is determined on the basis of a differential pressure change rate at a time of sensor measurement from the NOx removal rate with said SCR filter calculated by said NOx removal rate calculation unit, said differential pressure change rate being defined as the amount of increase in a converted differential pressure value normalizing the differential pressure of the exhaust gas across said SCR filter by the exhaust gas rate per unit increase in a filter PM deposition amount defined as the amount of particulate matter deposited in said SCR filter that is estimated on the basis of a parameter other than said converted differential pressure value, and said time of sensor measurement being defined as the time at which the measurement value of said NOx sensor used in calculation of the NOx removal rate by said NOx removal rate calculation unit is obtained; and a determination unit configured to determine that said exhaust gas purification system is faulty, if said corrected removal rate calculated by said corrected removal rate calculation unit is equal to or lower than a predetermined criterion removal rate that is determined on the assumption that particulate matter is not deposited in said SCR filter, wherein said corrected removal rate calculation unit makes said decrease larger in the case where said differential pressure change rate at said time of sensor measurement is lower than a predetermined threshold than in the case where said differential pressure change rate at said time of sensor measurement is equal to or higher than said predetermined threshold.

5. A fault diagnosis apparatus for an exhaust gas purification system according to claim 4, wherein in the case where said differential pressure change rate at said time of sensor measurement is lower than said predetermined threshold, a change in said decrease in calculation of said corrected removal rate by said corrected removal rate calculation unit relative to a change in said filter PM deposition amount at said time of sensor measurement is zero.

6. A fault diagnosis apparatus for an exhaust gas purification system according to claim 4, wherein in the case where said differential pressure change rate at said time of sensor measurement is lower than said predetermined threshold, said corrected removal rate calculation unit makes said decrease larger when the temperature of said SCR filter at said time of sensor measurement is low than when said temperature of said SCR filter at said time of sensor measurement is high.

* * * * *